United States Patent
Kinmon

(10) Patent No.: US 9,445,850 B2
(45) Date of Patent: Sep. 20, 2016

(54) INTRAMEDULLARY NAIL, SYSTEM, AND METHOD WITH DYNAMIC COMPRESSION

(71) Applicant: Kyle Kinmon, Boca Raton, FL (US)

(72) Inventor: Kyle Kinmon, Boca Raton, FL (US)

(73) Assignee: AFCN, LLC, Boca Raton, FL (US)

( * ) Notice: Subject to any disclaimer, the term of this patent is extended or adjusted under 35 U.S.C. 154(b) by 0 days.

(21) Appl. No.: 14/531,906

(22) Filed: Nov. 3, 2014

(65) Prior Publication Data

US 2015/0057663 A1    Feb. 26, 2015

Related U.S. Application Data

(63) Continuation of application No. 13/304,358, filed on Nov. 24, 2011, now Pat. No. 8,876,821.

(60) Provisional application No. 61/416,934, filed on Nov. 24, 2010.

(51) Int. Cl.
  *A61B 17/72*    (2006.01)

(52) U.S. Cl.
  CPC ....... *A61B 17/7241* (2013.01); *A61B 17/7225* (2013.01)

(58) Field of Classification Search
  CPC .......... A61B 17/7241; A61B 17/7216; A61B 17/7225; A61B 17/7233; A61B 17/72
  See application file for complete search history.

(56) References Cited

U.S. PATENT DOCUMENTS

| | | |
|---|---|---|
| 3,807,394 A | 4/1974 | Allenborough |
| 3,986,504 A | 10/1976 | Avila |
| 4,237,875 A | 12/1980 | Termanini |
| 4,621,629 A | 11/1986 | Koeneman |
| 4,644,943 A | 2/1987 | Thompson et al. |
| 4,875,475 A * | 10/1989 | Comte et al. .................. 606/64 |
| 4,959,064 A | 9/1990 | Engelhardt |
| 5,505,734 A | 4/1996 | Caniggia et al. |
| 5,658,287 A | 8/1997 | Hofman |
| 5,658,288 A | 8/1997 | Kim |
| 5,743,908 A | 4/1998 | Kim |
| 6,106,528 A * | 8/2000 | Durham et al. ................ 606/64 |
| 6,123,708 A * | 9/2000 | Kilpela et al. ................. 606/62 |
| 6,197,029 B1 | 3/2001 | Fujimori et al. |
| 6,270,499 B1 | 8/2001 | Leu et al. |

(Continued)

FOREIGN PATENT DOCUMENTS

WO     WO 0143652 A1 *  6/2001

OTHER PUBLICATIONS

Translation of WO 0143652 A1; accessed from EPO.org on May 3, 2015.*

*Primary Examiner* — Eduardo C Robert
*Assistant Examiner* — Julianna N Harvey
(74) *Attorney, Agent, or Firm* — Trojan Law Offices

(57) ABSTRACT

The present invention describes an intramedullary nail for use in orthopedic surgery for the fixation of bone fractures and fusion sites. The nail employs one or more internal loaded springs, biocompatible elastic or rubber bands, or other mechanism that provides continuous dynamic compression across the healing site throughout the healing process. By altering the size, tension and/or number of the internal compression devices, the amount of compression may be customized on a case-by-case basis. Further, the slots within the nail for its attachment can be utilized to create a torsional force when desired. The nail can have a cross-sectional shape that prevents its rotation. A system and method of use is also described.

12 Claims, 17 Drawing Sheets

(56) References Cited

U.S. PATENT DOCUMENTS

| | | |
|---|---|---|
| 6,579,293 B1 | 6/2003 | Chandran |
| 6,656,184 B1 | 12/2003 | White et al. |
| 6,736,819 B2 | 5/2004 | Tiperneni |
| 6,786,908 B2 | 9/2004 | Hover et al. |
| 7,410,488 B2 | 8/2008 | Janna et al. |
| 7,591,823 B2 | 9/2009 | Tiperneni |
| 7,601,153 B2 * | 10/2009 | Shinjo et al. ............... 606/64 |
| 7,695,471 B2 | 4/2010 | Cheung et al. |
| 7,776,038 B2 | 8/2010 | Prien |
| 7,942,876 B2 | 5/2011 | Hack |
| 7,947,043 B2 | 5/2011 | Mutchler |
| 2005/0101958 A1* | 5/2005 | Adam ............... 606/64 |
| 2007/0213725 A1 | 9/2007 | Hack |
| 2008/0147127 A1 | 6/2008 | Tiperneni et al. |
| 2008/0183171 A1* | 7/2008 | Elghazaly et al. ............... 606/64 |
| 2008/0221577 A1 | 9/2008 | Elghazaly |
| 2008/0243191 A1 | 10/2008 | Tiperneni |
| 2008/0294164 A1* | 11/2008 | Frank et al. ............... 606/64 |
| 2010/0010490 A1 | 1/2010 | Brigido |
| 2010/0249781 A1* | 9/2010 | Haidukewych et al. ....... 606/62 |
| 2010/0268285 A1 | 10/2010 | Tiperneni |

* cited by examiner

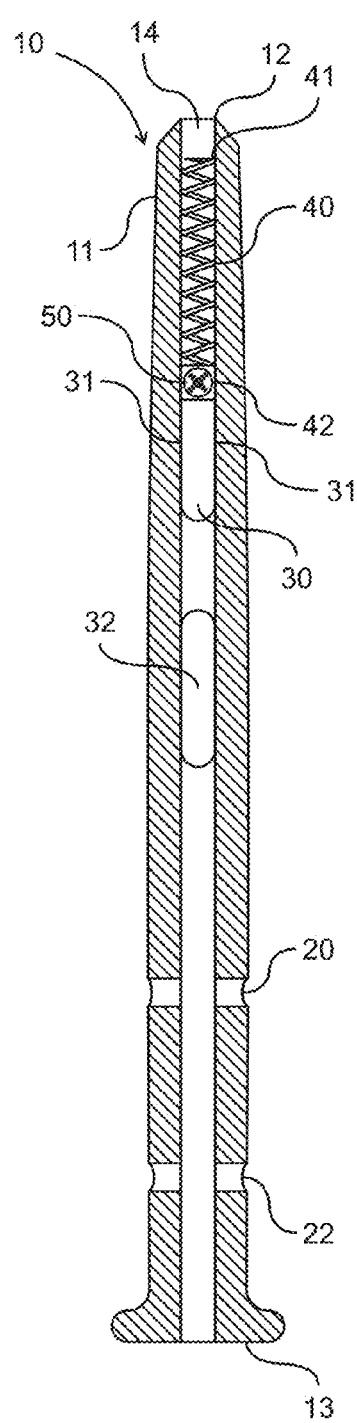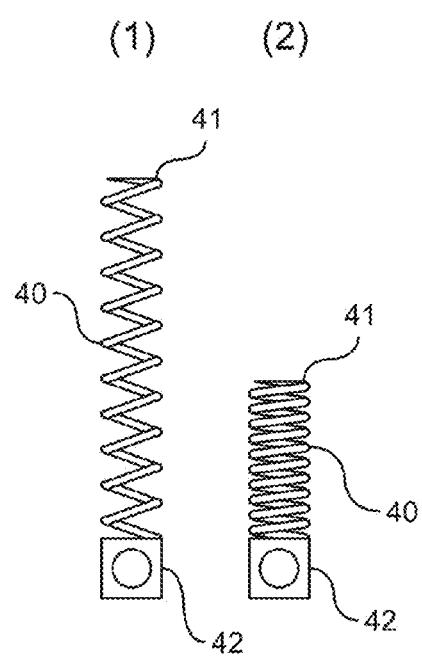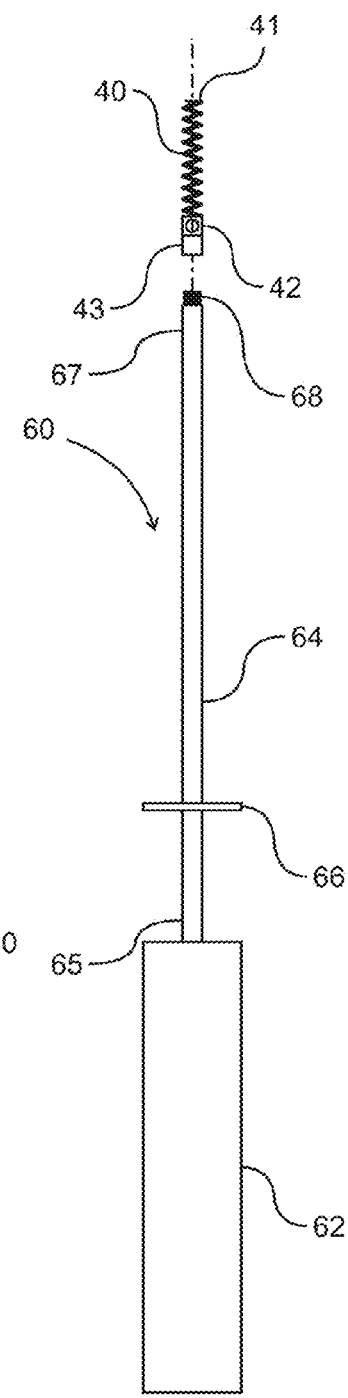
Fig. 8A
Fig. 8B
Fig. 8C

INTRAMEDULLARY NAIL, SYSTEM, AND METHOD WITH DYNAMIC COMPRESSION

CROSS-REFERENCE TO RELATED APPLICATIONS

The present application in a continuation of, and claims priority to, U.S. patent application Ser. No. 13/304,358, filed on Nov. 24, 2011, and issued as U.S. Pat. No. 8,876,821 on Nov. 4, 2014, which claims priority to U.S. Provisional Application Ser. No. 61/416,934, filed on Nov. 24, 2010, the contents of each are hereby incorporated by reference in their entireties.

BACKGROUND OF THE INVENTION (1) Field of the Invention

The present invention relates to an intramedullary nail with dynamic compression, and a system and method of use thereof.

(2) Description of the Related Art

To heal an injured bone properly, the bone must remain in stable position with the edges of the bone compressed against one another without motion. Intramedullary nails have been employed in orthopedic surgery for centuries to serve this purpose, as they are an excellent source of lasting axial and torsional stability, stiffness and rigidity. Intramedullary nailing has a long and interesting history that dates back to the 16th century. Küntscher developed modern intramedullary nailing techniques in Germany during the 1940s. The first transfixion interlocked nail was introduced in 1953, and intramedullary nailing has since become the standard of care for the treatment of fractures of long bone diaphyseal fractures such as those in the femoral shaft, tibia, humerus, and radius that require operative stabilization. Retrograde intramedullary nailing has also been used in the foot and ankle to perform arthrodesis of the tibia to the talus to the calcaneus, or the tibia to the calcaneus.

One objective of osteosynthetic implants is the anatomic reduction of the fracture. Another objective would be to minimize or eliminate interfragmentary motion. Still another objective involves increasing or maximizing blood supply to the fracture site by reducing or minimizing additional vascular damage. Sustained compressive therapy can also be osteoinductive, due to its piezoelectric effects on osteoblasts themselves. However, problems can arise when the bone fracture or fusion site is not sufficiently stabilized during the healing timeframe. Excessive interfragmentary motion results in the formation of fibrous, unmineralized scar tissue (resulting in a non-union or pseudo-arthrosis) versus the regeneration of bone. The unmineralized scar tissue is not load-supporting and skeletal function is lost. Compression prevents interfragmentary motion and stimulates the formation of bone. A sufficient blood supply must be maintained to support skeletal metabolism, bone regeneration, and remodeling of the fracture site.

The current standard of care includes osteosynthetic devices that are made of either stainless steel or titanium. The use of stainless steel or titanium in osteosynthetic devices has a long history and reasonable record of success. However, over time, the stainless steel and titanium fixation constructs (screws, plates and nails) do not maintain compression across the fracture fragments. This is due to the biological resorption that occurs across the fracture or fusion site during normal primary bone healing. The stiffness of these materials and the relative constructs initially serves well to maintain the healing bones in close compressed approximation to one another, but after re-absorption they actually serve to maintain the bones separated or distracted from one another. The reduction of compression of certain standard material plate and screw constructs is well known, has been studied, and is observed to be thirty-two percent (32%) over a two-week period. Intramedullary nails have shown a 90% reduction in compression with only one millimeter of resorption across the fusion site. As the necrotic surfaces of the fracture are resorbed, a non-load bearing gap develops between the fragments, thereby decreasing compression and increasing the risk of interfragmentary motion and scar tissue formation. Loss of compression is contrary to the objectives of fracture or fusion fixation in general, and osteosynthetic implants in particular. Improvements are needed which will maintain a compressive load across the fracture or fusion site over a longer period of healing, and in some cases assist in keeping the compressive load traverse to the line of the break.

The efficiency and effectiveness of intramedullary nailing can be considerably enhanced if the device provided continuous dynamic compression across the fracture or fusion site. This need for compression has been identified in the current art. However, many intramedullary nail systems include devices, both internal and external to the nail itself, which provide compression only at the time of insertion. The problem remains that during the healing process, re-absorption results in a gap across the healing site, and compression is lost.

Attempts have been made to allow dynamic compression with nails currently on the market and which are well known to the art. For example, in one attempt, proximal transfixion screws have been placed in slotted holes, which allow the distal segment of bone and the nail itself to slide proximally. But, the current nails are designed to allow this compression only after weight bearing has begun, employing the very ground reactive forces encountered during weight bearing itself to provide the necessary compression. Unfortunately, resorption occurs much earlier during the healing process than does weight bearing, especially in the many cases in which additional procedures such as mid-foot fusion, are performed simultaneously with rear-foot to ankle fusion. Therefore, in many cases, non-union has already occurred by the time weight bearing is allowed, i.e. the gap forms and fills in with fibrous tissue long before weight is born on the extremity, thereby preventing the formation of solid bone. Where the current art contains compression, it does not allow selection of compressive force and it couples compression with positioning of the nail, which can be detrimental to achieving proper positioning with the correct compression force desired.

The current art also describes a telescopic screw with an internal spring which is activated by turning the screw head and tightening of the screw. As the screw is inserted, the leading edge or threaded portion of the screw, which is the male member, advances, thereby loading the internal extension spring, thereby effectively producing compression across the fusion or fracture site. Unfortunately, multiple limitations are inherent in this design. First, the amount of compression is extremely variable and may be minimal, due to the fact that the spring is only loaded proportionate to the amount that the female end of the screw is extended. This is dependent on the amount of available space in the bone for screw insertion. Secondly, the fact that the screw length changes during screw insertion is problematic because with a fixed amount of bone available for screw insertion, the screw must be a precise and predictable length to ensure appropriate placement in the anatomy. If the female member of the screw encounters hard bone during insertion, the leading male member will prematurely extend, thereby altering the length of the screw. What is needed is a device with a predictable and reproducible length and a predictable and reproducible amount of compression.

The current art also describes a device which provides continuous compression through a hydraulic mechanism that is internal or external to the body and compresses the nail. This is problematic in that hydraulic fluid mechanisms are excessively complicated and not desirable for implantation. External mechanisms to provide compression of an intramedullary nail must violate the skin barrier and traverse to the bone, thereby presenting the likely possibility of superficial or deep infection.

Nitinol or memory metal nails have been described, but memory metal is also complicated in many cases, requiring the device to be delivered to the OR frozen, or heated with special machinery during implantation in order to activate the compression mechanism. Also, in order for a memory metal nail to compress, it would require that it also expand in thickness or diameter, which is not desirable in this application.

Other patents described in the prior art require lengthening of a screw to provide compression, including U.S. Pat. Nos. 4,959,064 and 6,656,184 disclose active compression mechanisms within a screw which utilize an extension spring. This is disadvantageous in that, as noted above, the amount of compression is extremely variable and may be minimal due to the fact that the compression is dependent on the amount of available space in the bone for screw insertion. A screw having a varying length that changes during screw insertion is also problematic because the screw should have a precise and predictable length to ensure appropriate placement in the anatomy, considering the fixed amount of bone available for screw insertion. The devices are also disadvantageous in that the screws only utilize extension springs to provide compression and cannot use different or multiple compression means simultaneously to achieve dynamic compression.

In addition to lack of continuous dynamic compression, a provision for rotational stability at the level of the fusion site is lacking with Intramedullary Nail systems currently described in the art. As previously mentioned, bones heal primarily when motion is minimized at the site of healing. Motion may occur through distraction, translation, bending or rotation. While translation and bending forces are controlled well with the current intramedullary nail systems, it is well known that rotation may occur, which may negatively impact bone healing. This rotation may occur at the fusion site because the current nails are round and the bones may rotate around the nail's axis. This problem can be addressed by employing a nail with a cross sectional shape which does not allow the bones to rotate around its axis. This shape is especially important at the level at or around the fusion sites, and in the areas where it traverses cortical or subchondral bone.

Therefore, what is needed in the art is a simple and reliable mechanism for achieving continuous dynamic compression with an intramedullary nail, which can be implanted within the nail itself, and avoids the use of hydraulic fluid, external mechanisms, weight bearing or memory metal. Specifically, an intramedullary nail that can actively engage a pin crossing the bone to provide continuous dynamic compression without weight bearing and can provide to the user a choice using of one or more compression mechanisms is needed. What is also needed is a device of a fixed size and length and will provide predictable and reproducible continuous dynamic compression across the fusion site from the time immediately following the surgical procedure throughout the healing process, including the six to twelve or more weeks spent without weight bearing, and can be easily adjusted to the compressive force that is desirable at the time of its installation. An intramedullary nail that includes a shape that does not allow rotation of the bone around the nail's axis is also needed.

With these goals in mind, the inventor has created an intramedullary nail with improved structural properties and compression capabilities, as well as an easy and effective insertion technique and system thereof for stabilizing bones with a intramedullary nail providing dynamic compression throughout the bone healing process.

BRIEF SUMMARY OF THE INVENTION

The present invention describes an intramedullary nail that provides continuous dynamic compression. The invention also describes a system for its insertion as well as a method for its insertion. In one embodiment, the intramedullary nail for providing dynamic compression across a fusion or fracture site comprises an elongated body having a proximal end, a distal end, and an inner channel. At least one distal aperture is located proximate to the distal end of the body and is capable of permitting a fastener to pass through it such that the fastener is secured in a position transversing the nail. At least one elongated aperture having interior sides is located closer to the proximal end of the body than the distal aperture and is capable of receiving a fastener that transverses the nail such that the nail may move relative to the fastener. The movement is restricted by the interior sides of the elongated aperture.

The nail also comprises at least one compression member that is contained within the inner channel, the compression member having a first end and a second end, and at least one of the ends is capable of engaging the fastener received in at least one elongated aperture. The compression member may exert a force to move the nail relative to the fastener, while the movement is restricted by the interior sides of the elongated aperture. The intramedullary nail can thereby provide compression to the fusion or fracture site when at least one fastener is received in the elongated aperture on one side of the fusion or fracture site and at least one fastener is received in the distal aperture on an opposing side of the fusion or fracture site. The at least one compression member can be a compression spring, an extension spring, a torsional spring, an elastic band, a Belleville washer, a plurality of Belleville washers, or any combination thereof.

In one embodiment, the intramedullary nail further comprises a first and a second distal aperture, a first and a second elongated aperture, and a first and a second compression member. The first end of the first compression member abuts the proximal end of the nail and the second end of the first compression member is capable of engaging a fastener received in the first elongated aperture. The first end of the second compression member is capable of engaging a fastener received in the second elongated aperture and the second end of the second compression member is capable of engaging a fastener received in the first distal aperture. Both the first and second compression member can exert a force to move the nail and thereby provide compression to a fusion or fracture site located between the first distal aperture and the second elongated aperture when the fasteners are received in the nail. The first compression member can be a compression spring, a torsional spring, a Belleville washer, or a plurality of Belleville washers, while the second compression member can be an extension spring, biocompatible rubber, compressed gas compartment, elastic band, or any stretch-activated compression member.

In another embodiment, the nail further comprises a projection, wherein the projection is located within the inner channel between a first elongated aperture and a second elongated aperture. The first end of a first compression member abuts the proximal end of the nail and the second end of the first compression member is capable of engaging a fastener received in the first elongated aperture. The first end of a second compression member abuts the projection and the second end of the second compression member is capable of engaging a fastener received in the second elongated aperture. Both of the first and second compression member can exert a force to move the nail and thereby provide compression to a fusion or fracture site located between the first distal aperture and the second elongated aperture when the fasteners are received in the nail. The first compression member can be a compression spring, a torsional spring, a Belleville washer, or a plurality of Belleville washers, and the second compression member is can be a compression spring, a torsional spring, a Belleville washer, or a plurality of Belleville washers.

The nail can further comprise a third compression member. The first end of the third compression member is capable of engaging the fastener received in the second elongated aperture and the second end of the third compression member is capable of engaging a fastener received in the first distal aperture. In this embodiment, the first, second, and third compression member can exert a force to move the nail and thereby provide compression to a fusion or fracture site located between the first distal aperture and the second elongated aperture when the fasteners are received in the nail. The first compression member can be a compression spring, a torsional spring, a Belleville washer, or a plurality of Belleville washers, the second compression member can also be a compression spring, a torsional spring, a Belleville washer, or a plurality of Belleville washers, and the third compression member can be an extension spring, biocompatible rubber, compressed gas compartment, elastic band, or any stretch-activated compression member.

In another embodiment, the nail comprises one compression spring, wherein the first end of the compression member abuts the proximal end of the nail and the second end of the compression member is capable engaging a fastener received in at least one elongated aperture. The compression member exerts a force to move the nail and thereby provide compression to a fusion or fracture site located between at least one distal aperture and the elongated aperture when fasteners are received in the nail. The compression member can be a compression spring, a torsional spring, a Belleville washer, or a plurality of Belleville washers.

In yet another embodiment, the nail comprises one compression spring, wherein the first end of the compression member is capable of engaging a fastener received in at least one elongated aperture and the second end of the compression member is capable of engaging a fastener received in at least one distal aperture. The compression member exerts a force to move the nail and thereby provide compression to a fusion or fracture site located between the distal aperture and the elongated aperture when the fasteners are received in the nail. The compression member can be an extension spring, biocompatible rubber, compressed gas compartment, elastic band, or any stretch-activated compression member.

In another embodiment, the intramedullary nail comprises an elongated body having two independent body sections comprising a proximal section and a distal section. The distal section is at least partially contained within the proximal section. The proximal section comprises an inner channel and at least one aperture capable of permitting a fastener to pass through the proximal section and be secured in a position transversing the nail. The distal section comprises an inner channel and at least one aperture capable of permitting a fastener to pass through the distal section and be secured in a position transversing the nail. The nail also comprises a compression member contained within both the inner channel of the proximal section and the inner channel of the distal section, the compression member having a first end and a second end, wherein the first end is capable of engaging a fastener received in the aperture of said proximal section and the second end is capable of engaging a fastener received in the aperture of the distal section, wherein the compression member may exert a force to move the proximal section and the distal section toward one another. The intramedullary nail can thereby provide compression to the fusion or fracture site when at least one fastener is received in the aperture of the proximal section on one side of the fusion or fracture site and at least one fastener is received in the aperture of the distal section on an opposing side of the fusion or fracture site. The compression member and distal section can optionally be made as one unit. The compression member can be an extension spring, biocompatible rubber, compressed gas compartment, elastic band, or any stretch-activated compression member.

Each of the foregoing embodiments can also comprise an appropriate number of fasteners to anchor the nail to the bone and engage with the one or more compression members. All of the foregoing embodiments can also have at least one distal aperture capable of permitting a fastener to pass through it at an oblique angle and be secured in a position transversing the nail. A compression member can also be capable of engaging the fastener received at an oblique angle in the distal aperture. In addition, the elongated and distal apertures of the nail can have axes transversing the nail that are parallel or perpendicular with one another. The elongated body of all embodiments of the nail can have a cross-sectional shape that provides rotational stability to the nail. For example, the cross-sectional shape can be an oval, triangle, cruciate shape, partially oval, clover shape, star shape, trapezoidal, rhomboid, or any other irregular geometric shape.

An intramedullary nail system comprising is also disclosed, including any of the aforementioned intramedullary nails, and an insertion device to insert the at least one compression member into the nail. The insertion device comprises a handle and a rod. The rod has a first end, a second end, and a stop member projecting from the rod, the first end is connected with the handle, and said second end is capable of engaging with at least one compression member. The whereby said at least one compression member can engage the second end of the insertion device and can be inserted in the channel from the distal end of the nail such that the stop member will stop the insertion device during insertion into the nail at a position within the nail to align the at least one compression member with the at least one distal aperture or the at least one elongated aperture. The second end of the insertion device can further comprise a threaded portion to engage with a corresponding threaded portion formed on an end of a compression member. The system can also include the appropriate number of fasteners to transverse through the nail at a perpendicular or oblique angle to the longitudinal axis of the nail.

A method for using the cannulated intramedullary nail to provide compression across a fusion or fracture site is also disclosed. One method comprises the acts of selecting an intramedullary nail comprising an elongated nail body, the elongated nail body comprising a proximal end, a distal end, an inner channel, at least one distal aperture located proximate to the distal end, and at least one elongated aperture located closer to the proximal end than the distal aperture, the at least one elongated aperture having a proximal end and a distal end; inserting the intramedullary nail across a fusion or fracture site such that the distal aperture is on one side of the fusion or the fracture site and the elongated aperture is on an opposing side of the fusion or the fracture site; selecting at least one compression member having a first end and a second end, wherein at least one of the ends is capable of engaging a fastener; inserting the compression member into the channel of nail such that the end of the compression member that is capable of engaging a fastener is aligned with one of the at least one elongated aperture; inserting at least one fastener through the at least one elongated aperture aligned with the at least one compression member, wherein is engaged with the at least one compression member; and inserting at least one fastener through the at least one distal aperture. The method can also include the act of inserting a fastener through a second elongated aperture and inserting a fastener through a second distal aperture.

The method can be modified to comprise acts for inserting one compression member, two compression members, or three compression members as described in further detail herein. The one or more compression members utilized can have different mechanism of providing compression.

BRIEF DESCRIPTION OF SEVERAL VIEWS OF THE DRAWINGS

FIG. 8A is a partially cut-away view of a nail according to the present invention;

FIG. 8B is an illustration of a compression member according to the present invention;

FIG. 8C is an illustration of an insertion tool according to the present invention;

DETAILED DESCRIPTION OF THE INVENTION

Figure 1:
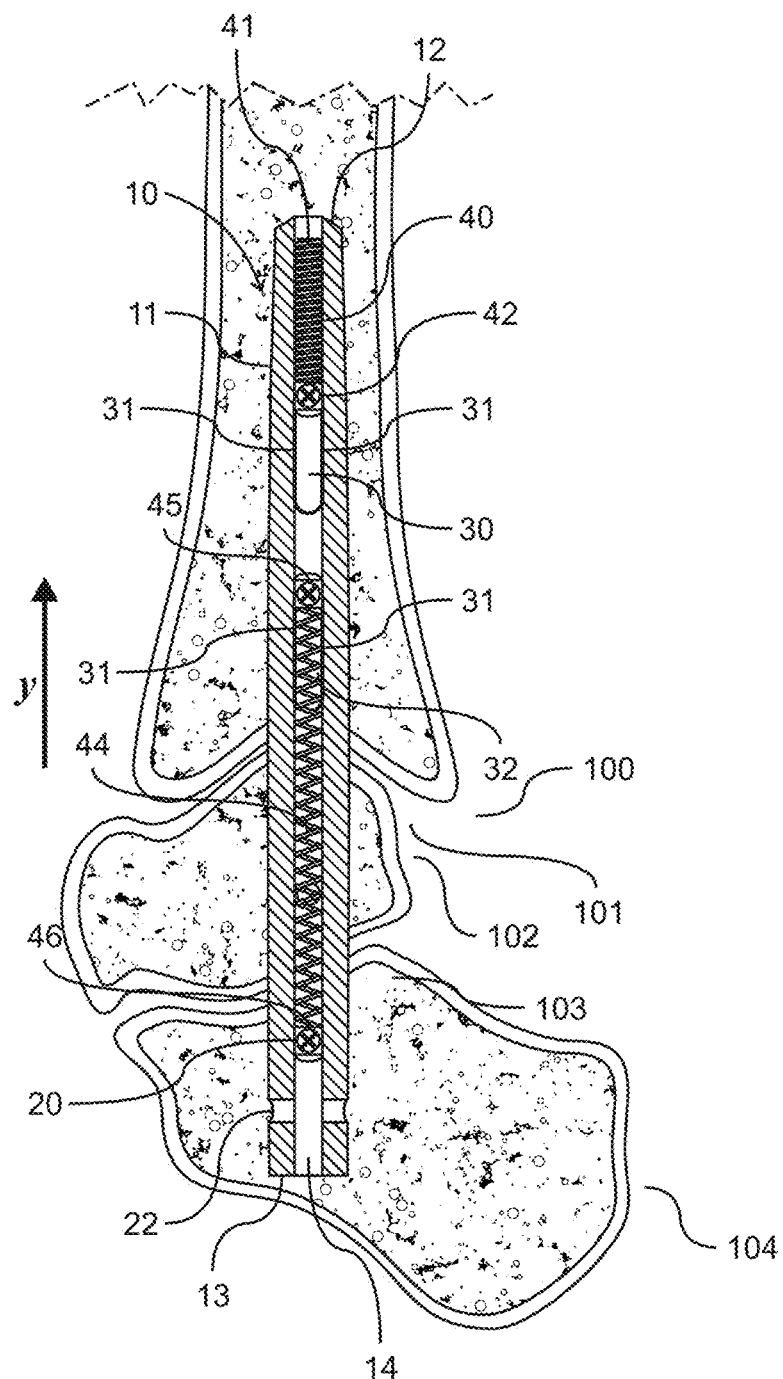
FIG. 1 is a cross-sectional view of a nail and compression member according to the present invention and an example of a surgical placement thereof.

The present invention overcomes disadvantages of the prior art, as identified and disclosed by the inventor, by providing a cannulated intramedullary nail and steps for its insertion so that continuous dynamic compression is applied across a fusion or fracture site. Continuous dynamic compression is accomplished through the employment of one or more mechanical compression members, such as compression or extension springs or biocompatible elastic or rubber bands, which are loaded into the cannulated canal of the nail itself. The compression mechanism is engaged with transfixion interlocking fasteners such as pins, rods, or screws that are inserted across the nail.

The detailed description set forth below in connection with the appended drawings is intended to provide example embodiments of the present invention and is not intended to represent the only forms in which the invention may be constructed or utilized. The description sets forth the functions and the sequences of steps for constructing and operating the invention. However, it is to be understood that the same or equivalent functions and sequences may be accomplished by different embodiments that are also intended to be encompassed within the spirit and scope of the invention.

Some embodiments of the invention will be described in detail with reference to FIGS. 1-17. Additional embodiments, features, and/or advantages of the invention will become apparent from the description or may be learned by practicing the invention. The drawings in the figures are not necessarily drawn to scale and have like numerals referring to like features through both the drawings and the description.

The nail 10 shown in the figures has a smooth exterior surface however there is no requirement for a smooth surface. The nail can be made of suitable material known in the art and constructed with various textures or irregular shape to keep it in position. For example, the nail 10 can have a roughened exterior surface or an exterior surface having dimples or cleats as appropriate for the particular application. The nail body 11 can have one of the following cross sectional shapes, or any other shape which does not allow rotation at the fusion site, at any contact with subchondral or cortical bone which it traverses, or along its entire length: oval, triangle, cruciate (sharp or round angles), partially oval, clover shape, star shaped, trapezoidal, rhomboid, etc. The body 11 of the nail 10 can also be configured in sections that allow each section to ride over the adjacent section using any conventional methods for interlocking such as rods, pins or snaps.

The nail 10 has an elongated nail body 11 having a proximal end 12, a distal end 13, and an inner channel 14. The inner channel 14 can be formed through the entire nail 10 from the proximal end 12 to the distal end 13 such that a hole can be formed at each end to accommodate a guide wire if a guide wire is used to guide the insertion of the nail 10. However, the channel 14 need not form a hole at each end in every embodiment of the nail 10. The nail 10 can have one or more compression members that fit within the inner channel 14. In addition, the nail 10 has at least one elongated aperture 30 therethrough to accommodate a fastener in which the fastener is simultaneously transversing the nail 10 to anchor the nail 10 to one side of a fusion or fracture site while engaging a compression member 40 contained within the inner channel 14 of the nail 10. The nail 10 also has at least one distal aperture 20 located proximate to the distal end 13 of the nail body 11 to secure a fastener in a position transversing the nail 10 to anchor the nail 10 to the other side of the fusion or fracture site.

The compression member 40 can exert a force to move the nail 10 relative to the fastener within the elongated aperture 30 such that the interior sides 31 of the elongated aperture 30 restrict the movement of the nail 10. Thus, when the nail 10 is moved by the force of the compression member 40, the nail 10 can provide compression to the fusion or fracture site when at least one fastener is engaged with the compression member 40 and is received in the elongated aperture 30 on one side of the fusion or fracture site and at least one fastener is received in the distal aperture 20 on the other side of the fusion or fracture site.

The particular structure of the present invention provides advantages over the prior art which are not obvious variations to one of ordinary skill in the art. Unlike the prior art, the one or more compression members 40 within the nail 10 of the present invention can actively engage a fastener crossing the bone to provide dynamic compression and reduce a fracture or fusion site. The nail 10 is of a fixed size and length and will provide predictable and reproducible continuous dynamic compression across the fusion site from the time immediately following the surgical procedure throughout the healing process, including the six to twelve or more weeks spent without weight bearing and can be easily adjusted to the compressive force that is desirable at the time of its installation. The compressive force desired can be easily adjusted by selection of the appropriate compression member 40 by virtue of its construction and modulus of elasticity. The structure of the intramedullary nail 10 of the present invention can also provide versatility in that it allows a surgeon to choose among a variety of compression mechanisms to apply continuous dynamic compression to a fusion site or fracture while the prior art does not.

The one or more compression members 40 of the present invention include, but are not limited to, a compression, extension or torsional spring, or may include Belleville washers either singular, parallel, in series, biocompatible rubber, elastic band, compressed gas compartment, or a combination of any the above. A surgeon can choose to place one or more of the above compression members 40 within the body 11 of the nail 10. In the alternative, the one or more compression members 40 may be preloaded in the nail 10.

Regarding the different types of compression members 40, an extension spring is designed to operate with a tension load while a compression spring is designed to operate with a compression load. The extension spring stretches as the load is applied to it and the compression spring is shortened as the load is applied to it. A torsion spring, unlike the extension and compression spring types in which the load is generally an axial force, is designed to operate with a torque or twisting force. The end of a torsion spring rotates through an angle as the load is applied. A Belleville washer is type of spring shaped like a washer. It has a frusto-conical shape which gives the washer a spring characteristic. Multiple Belleville washers may be stacked to modify the spring constant. The device can also use biocompatible elastics.

The compression member may be made of materials such as but not limited to stainless steel, nitinol or other memory metal, titanium, biodur, etc. In the embodiments in which one or more compression member 40 is an elastic band, the compression member may be constructed of a material which is biocompatible, non-resorbable and non-biodegradable. Specific materials which may be used to construct the band include, but are not limited to, dacroncrystalline polypropylene, polyethylene, polyester fiber, PLLA, PDLA, polyurethane, nylon, titanium mesh, silicon, silastic and other polymers. In certain embodiments, the compression member 40 can be elastic and/or reversible.

The one or more compression members 40 are attached to one or more fasteners transversing the nail 10 in different configurations 10. The loaded compression member 40 can exert a compressive force to move the nail 10 relative to the fastener transversing the nail 10, in which the movement of the nail 10 is restricted by the interior sides 31 of the one or more elongated apertures 30. The nail 10 can actively engage any of the foregoing compression members 40 with fasteners such as pins, rods, or screws, etc., that traverse the intramedullary nail 10 to anchor the nail 10 and simultaneously provide compression to the desired surgical area. Throughout the description of the invention herein, the term "fastener" shall mean a screw, nail, pin, rod, or any other equivalent structure known in the art.

At least one end 41, 42 of the compression member 40 and a fastener can engage with one another in a variety of manners known in the art. In most of the embodiments shown, the compression member 40 has an aperture 47, 48 through at one or more end 41, 42 of the compression member 40 to receive the fastener therethrough. This is just one embodiment in which the compression member 40 is actively engaged with the fastener and the illustrated embodiments are not meant to be limiting. A compression member does not require a certain specific structure to engage a fastener. For example, a compression spring 40 can engage a fastener merely by abutting and exerting a driving force on the fastener. Thus, the compression member 40 can engage with a fastener that transverses the nail 10 in any manner known in the art or disclosed herein.

The nail 10 includes one or more elongated apertures 30 in which a fastener may pass through to transverse the nail 10. The fastener placed in each elongated aperture 30 pierces both sides of the bone on each side of the nail 10. In other words, a fastener can be inserted through one side of the bone, through the elongated aperture 30 in the nail 10, and into the other side of the bone. Each proximal transfixion fastener can change position within the respective elongated aperture 30 when the nail 10 moves, thus creating a dynamic operation of the nail 10 with respect to the fastener. The nail 10 also includes one or more apertures 20 at the distal end 13 of the nail 10. These distal apertures 20 are not elongated in shape and do not allow movement of the nail 10 with respect to fasteners inserted therethrough, thus creating a static position of the fastener with the nail 10. One or more fasteners can be placed in the one or more apertures 20 at the distal end 13 of the nail 10 to anchor the nail 10 to the bone.

The elongated apertures 30 of the nail 10 that can receive the fasteners can also follow the curvature of the nail 10, which will create a torsional force on the bone due to the cam action between the elongated aperture 30 and the screw. The elongated apertures 30 shown in the nail 10 can be parallel to the long axis of the nail 10 or can be cut at an angle creating a camming effect that causes a torsion force being placed across the fusion site.

It should also be noted that distraction and rotational instability is further controlled with the internal dynamic compression mechanism inherent in this nail system. The one or more compression member 40 will counteract any tendency for distraction at the fusion site during healing by nature of their desire to compress. The one or more compression member 40 will also indirectly lend rotational and translational stability through friction created with compression.

FIG. 1 is an overview of one embodiment of the intramedullary nail 10 utilizing two compression members and an example placement of the nail 10 inserted across the calcaneus, talus, and tibia. While the invention described herein is shown for foot and ankle surgical procedures, this invention is not limited to that particular area of the anatomy, and can be used throughout all areas of the human and animal body and skeleton.

The nail 10 includes a first elongated aperture 30 and a second elongated aperture 32, each of which having interior sides 31. As a non-limiting example, the elongated apertures 30, 32 shown in FIG. 1 are oblong slots penetrating through the nail 10. The nail 10 also includes a first distal aperture 20 and a second distal aperture 22. The compression member 40, 44 inserted or pre-loaded in the inner channel 14 of the nail 10 may be comprised of, but not limited to, two separate spring-type mechanisms. More specifically, in the embodiment shown in FIG. 1, the nail 10 includes a first compression member 40 and a second compression member 44, each of which having a first end 41, 45 and a second end 42, 46. As shown in FIG. 1, the first end 41 of the first compression member 40 abuts the proximal end 12 of the nail 10 and the second end 42 of the first compression member 40 is capable of engaging a first fastener 50 received in a proximal end 33 the first elongated aperture 30. The first end 45 of the second compression member 44 is capable of engaging a second fastener 51 received in the proximal end 33 of the second elongated aperture 32 and the second end 46 of the second compression member 44 is capable of engaging a third fastener 52 received in the first distal aperture 20. Both the first 50 and second 51 fasteners are inserted through the most proximal ends 33 of each of the first 30 and second 32 elongated apertures and engage the first ends 41, 45 of each first and second compression members 40, 44 as the fasteners 50, 51 pass through the respective first and second elongated apertures 30, 32. A fourth fastener 53 can be inserted through the second distal aperture 22 to further anchor the nail 10 to the bone. As shown, the second distal aperture 22 has an axis 92 transversing the nail 10 in a direction perpendicular to the transversing axes 90 of the first and second elongated apertures 30, 32 and the first distal aperture 20. In other embodiments, both the first and second distal apertures 20, 22 can have axes 92 transversing the nail 10 in a direction perpendicular to the transversing axes 90 of the first and second elongated apertures 30, 32.

As shown in FIG. 1, the first fastener 50 is locked in place in the tibia 100 while the compressive force of the first compression member 40 moves the nail 10. The nail 10 movement is guided by the first fastener 50 inserted through the first elongated aperture 30 and engaged with the first compression member 40. The second fastener 51 is also locked in place in the tibia 100 while the third fastener 52 is inserted into the calcaneus 104 through the first distal aperture 20. Alternatively, the third fastener 52 can be inserted into the talus 102 through the first distal aperture 20. However, as noted above, the compression member can span across any fusion site or fracture site and need not be limited to applications across tibia talar joint fusion sites 101 and sub talar joint fusion sites 103. The compressive force of the second compression member 44 between the second 51 and third fastener 52 also moves the nail 10, and the nail 10 movement is guided by the second fastener 51 inserted through the second elongated aperture 32. As shown in FIG. 1, the nail 10 moves in the direction "y", which is toward the proximal end 12 of the nail 10. As a result, the fasteners 50, 51 will change position from the proximal ends 33 of the elongated apertures 30, 32 to the distal ends 34 of the elongated apertures 30, 32. Thus, compression is applied to the tibia talar joint fusion site 101 between the tibia 100 and talus 102 and the sub talar joint fusion site 103 between the talus 102 and calcaneus 104.

In the embodiment shown in FIG. 1, the first compression member 40 shown can be a compression spring, torsional spring, Belleville washer or multiple Belleville washers in a parallel or series configuration, or a combination thereof, inserted and compressed or activated between the proximal end 12 of the nail 10 and a first fastener 50 in the first elongated aperture 30 that is closest to the proximal end 12 of the nail 10. The second compression member 44 can be an extension spring, biocompatible rubber, compressed gas compartment, or elastic band, or other similar mechanism that can be loaded and stretch activated between a second locking fastener 51 in the center most second elongated slotted hole 32 of the nail 10 and a third locking fastener 52 in the center most first distal aperture 20 of the nail 10.

A constant predictable compression can be applied to the proximal end 12 of the nail 10 by the first compression member 40, which will effectively apply constant compression to the fusion site. In the particular embodiment shown in FIG. 1, the compression member 40 pushes on the proximal end 12 of the nail 10 further into the tibia 100 and the nail 10 slides over the first fastener 50 that is locked in the tibia 100 via the first elongated slotted aperture 30. The compression member 40 effectively pulling the calcaneus 104 up against the talus 102, and the talus 102 up against the tibia 100, causing compression at both the tibia talar joint fusion site 101 and the sub talar joint fusion site 103.

The second compression member 44 crosses the intended site of compression and applies constant predictable compression to that site. As shown in FIG. 1, the second compression member 44 can be an extension spring. The extension spring pulls the nail 10 in the proximal direction via the third distal locking fastener 52 affixing the nail 10 to the calcaneus 104, effectively causing compression to both fusion sites 101, 103. Overall, both the first and second compression members 40, 44 move the nail 10 inside the tibia 100, applying compression to both fusion sites 101, 103.

Figure 16:
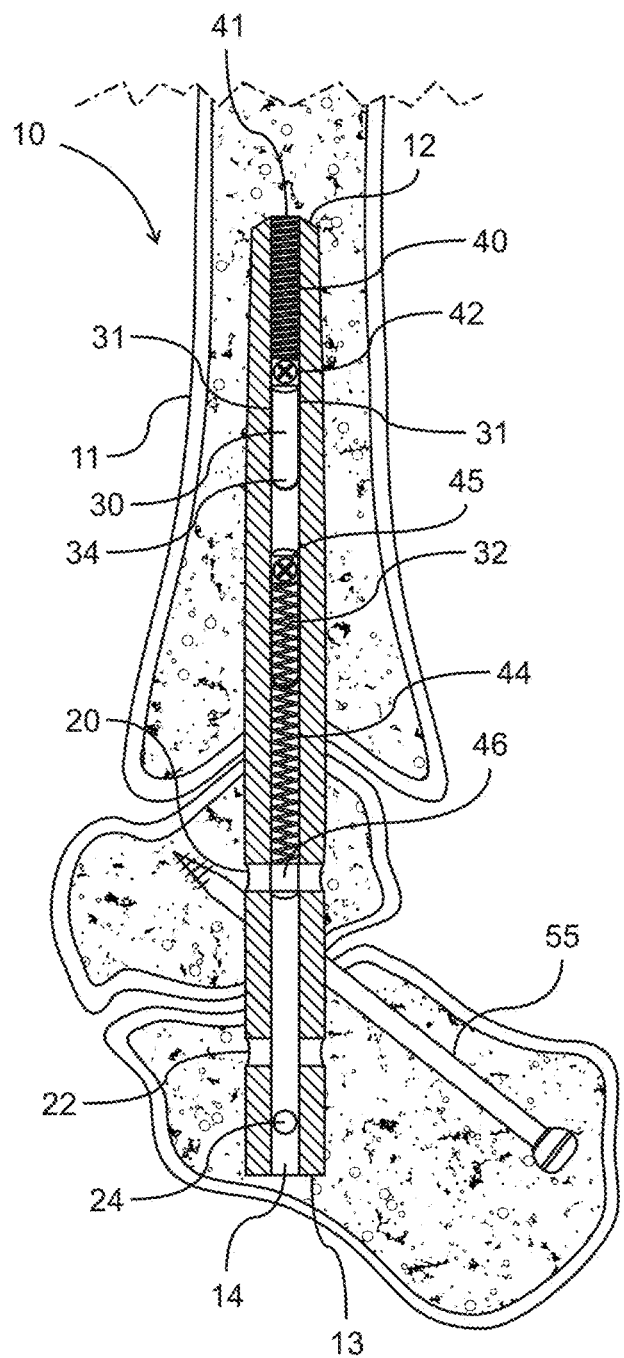
FIG. 16 is a cross-sectional view of a nail and oblique screw according to the present invention and an example of a surgical placement thereof.

In addition, the surgeon has the option of inserting a fastener 55 in an oblique direction from the calcaneus into the talus, traversing the sub talar joint. This embodiment provides additional rotational stability and static compression across the subtalar joint, but would sacrifice continuous dynamic compression across the subtalar joint. As shown in FIG. 16, the fastener 55 can be inserted in an oblique direction and proximate to the nail 10. Any embodiment of the nail 10 utilizing one or more compression members 40 described herein may be used in conjunction with a fastener inserted proximate to the nail at an oblique angle 55, i.e., the nail 10 is not limited to the embodiment shown in FIG. 16. In such embodiments, one or more compression members 40 such as a compression spring, an extension spring, or a combination thereof, can provide continuous dynamic compression across the ankle joint.

Figure 17:
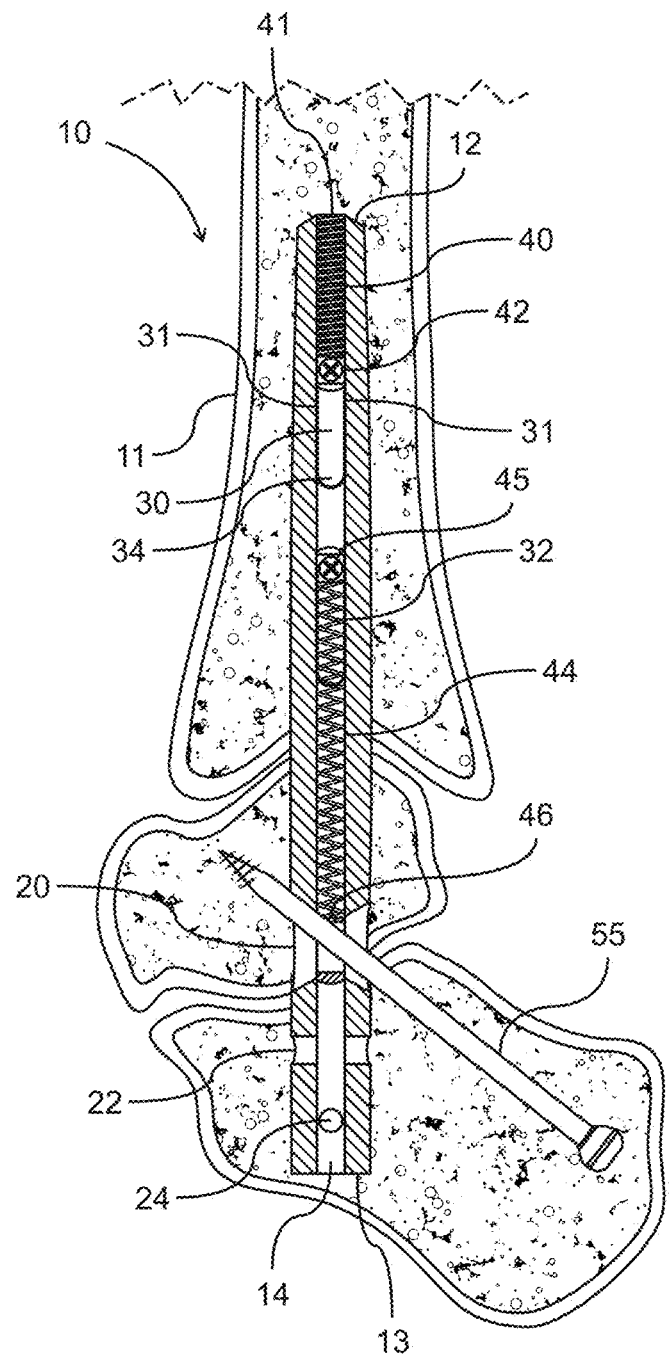
FIG. 17 is a cross-sectional view of a nail accommodating an oblique screw according to the present invention and an example of a surgical placement thereof.

Alternatively, as shown in FIG. 17, at least one distal aperture 20, 22 is capable of permitting a fastener 55 to pass therethrough at an oblique angle and be secured in a position transversing the nail 10. A compression member can engage the fastener 55 placed at an oblique angle. As a non-limiting example, a fastener 55 such as a subtalar screw can be engaged with an extension spring in a distal aperture 20. One or more compression members 40, 44 can be utilized in this embodiment and the fastener 55 passing through at least one distal aperture 20, 22 at an oblique angle need not engage the one or more compression members 40, 44. For example, the nail 10 can utilize one compression spring, two compression springs, one compression spring and one extension spring, or two compression springs and one extension spring, wherein the extension spring can engage the fastener 55 at an oblique angle to the nail in a distal aperture 20, 22, or engage a fastener 52 transversing the nail at a perpendicular angle to the nail in a distal aperture 20, 22.

Figure 2:
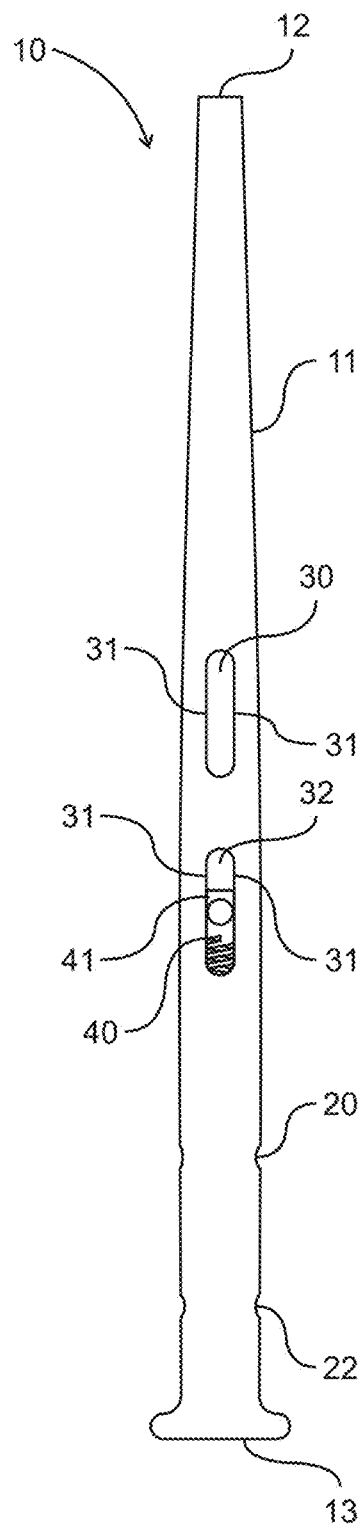
FIG. 2 is a longitudinal perspective view of a nail according to the present invention.

A longitudinal view of another embodiment of the nail 10 is shown in FIG. 2. In the embodiment shown, the nail 10 has a first elongated aperture 30 and a second elongated aperture 32 for insertion of a first and second fastener 50, 51 in a direction transverse to the nail 10. The fasteners 50, 51 pierce the bone on both sides of the bone in relation to the nail 10. These elongated apertures 30, 32 create a dynamic portion of the nail 10 in that they allow movement of the nail 10 with respect to the transverse fasteners. Also shown in FIG. 2 is placement of a compression member 40, i.e., a spring, within the nail 10 such that the proximal first end 41 of the compression member 40 is aligned with the second elongated aperture 32 that is closest to the nail head 13. The compression member 40 shown has a hole at its leading first end 41 to receive a fastener that traverses the nail 10 and bone once inserted. The compression member 40 can engage the fastener in any other manner known in the art. The first elongated aperture 30 can be transversed by a fastener which can be locked in place in the bone. When the second distal end 42 of the compression member 40 is put into place utilizing a fastener in the first locking hole 20 in the distal end 13 of the nail body 11, shown in FIG. 3, the compression member 40 can place a dynamic compressive force across a fusion site located between the dynamic second elongated aperture 32 and the first locking distal aperture 20.

Figure 3:
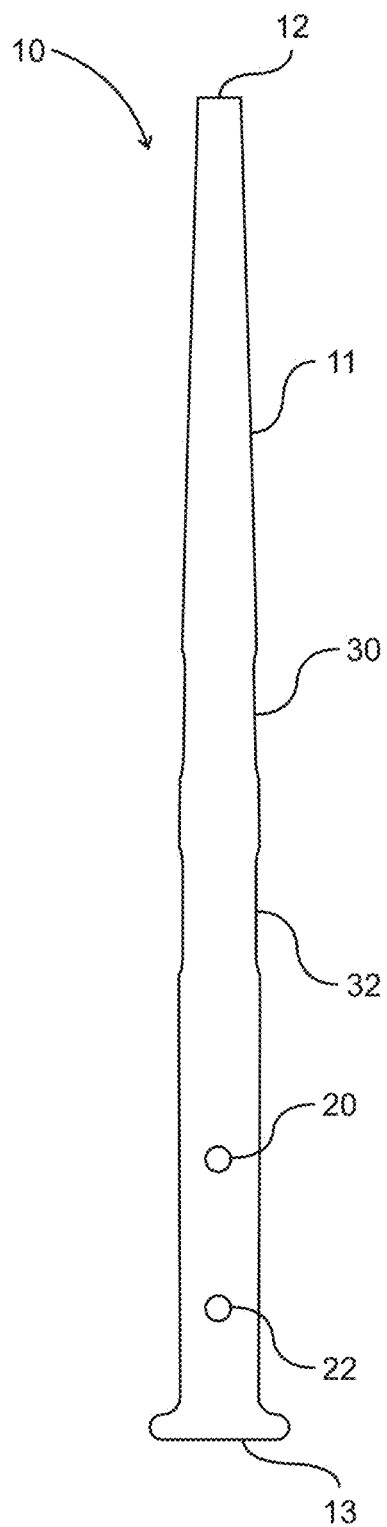
FIG. 3 is a longitudinal perspective view of the nail shown in FIG. 2 rotated 90° around the vertical axis according to the present invention.
Figures 9A, 9B, 9C:
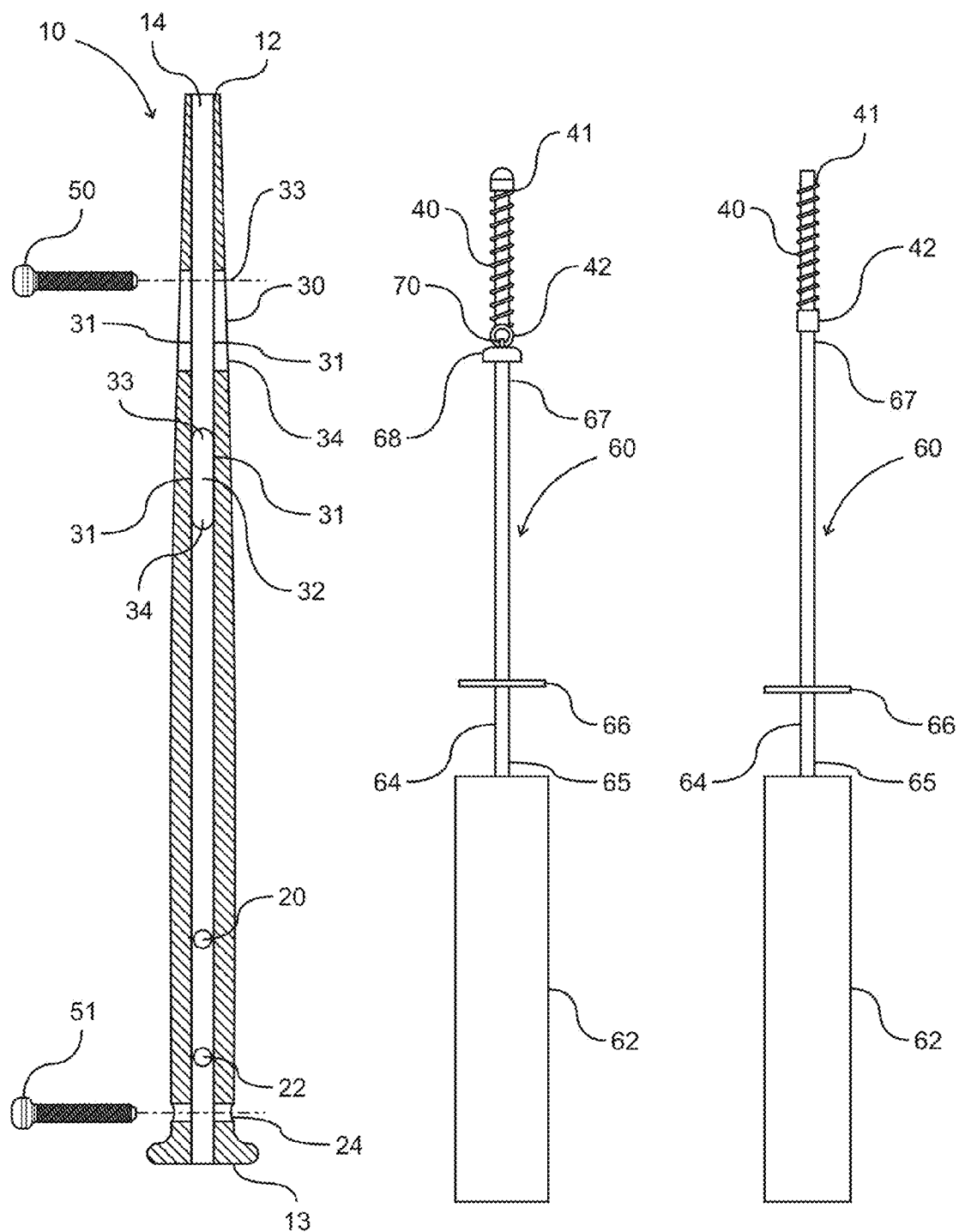
FIG. 9A is a partially cut-away view of a nail system according to the present invention.
FIG. 9B is an insertion tool according to the present invention.
FIG. 9C is another embodiment of an insertional tool according to the present invention.

FIG. 3 illustrates the nail 10 embodiment shown in FIG. 2 rotated ninety degrees around the vertical axis showing an embodiment of two round distal "locking" apertures 20, 22 through the body of the nail 10, toward the distal end 13 or head end of the nail 10. In this embodiment, the axes 92 of the distal apertures 20, 22 running transverse through the nail 10 are substantially perpendicular to the axes 90 of the elongated apertures 30, 32, also running transverse through the nail 10. A fastener can be inserted in the second distal aperture 22 closest to the distal end 13 of the nail 10 to anchor the nail 10 and another fastener can be inserted through the first distal aperture 20 to anchor a second end 42 of the compression member 40 that supplies the compressive force. The nail 10 can utilize one or more of the elongated apertures 30 and one or more of the distal apertures 20. In addition, the axes 90 of one or more elongated apertures 30 and the axes 92 of one or more distal holes 20 can be parallel and aligned on the nail body 11 with each other rather than having substantially perpendicular transverse axes, as described in other embodiments herein. As shown in FIG. 9A, the axes 90 of the one or more elongated apertures 30, 32 need not run in the same direction as each other, nor do the axes 92 of the one or more distal apertures 20, 22, 24.

Figure 4:
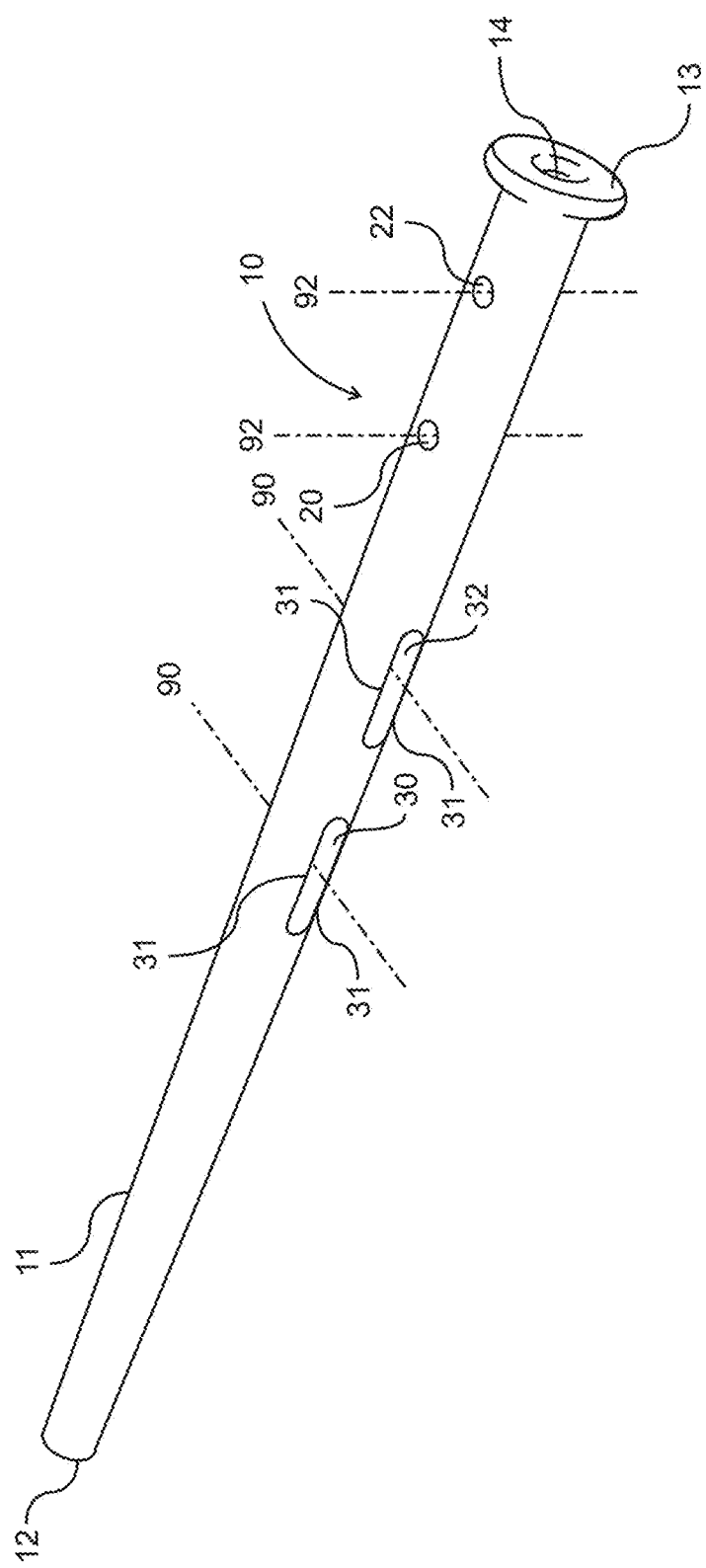
FIG. 4 is a perspective view of a nail according to the present invention.
Figure 5:
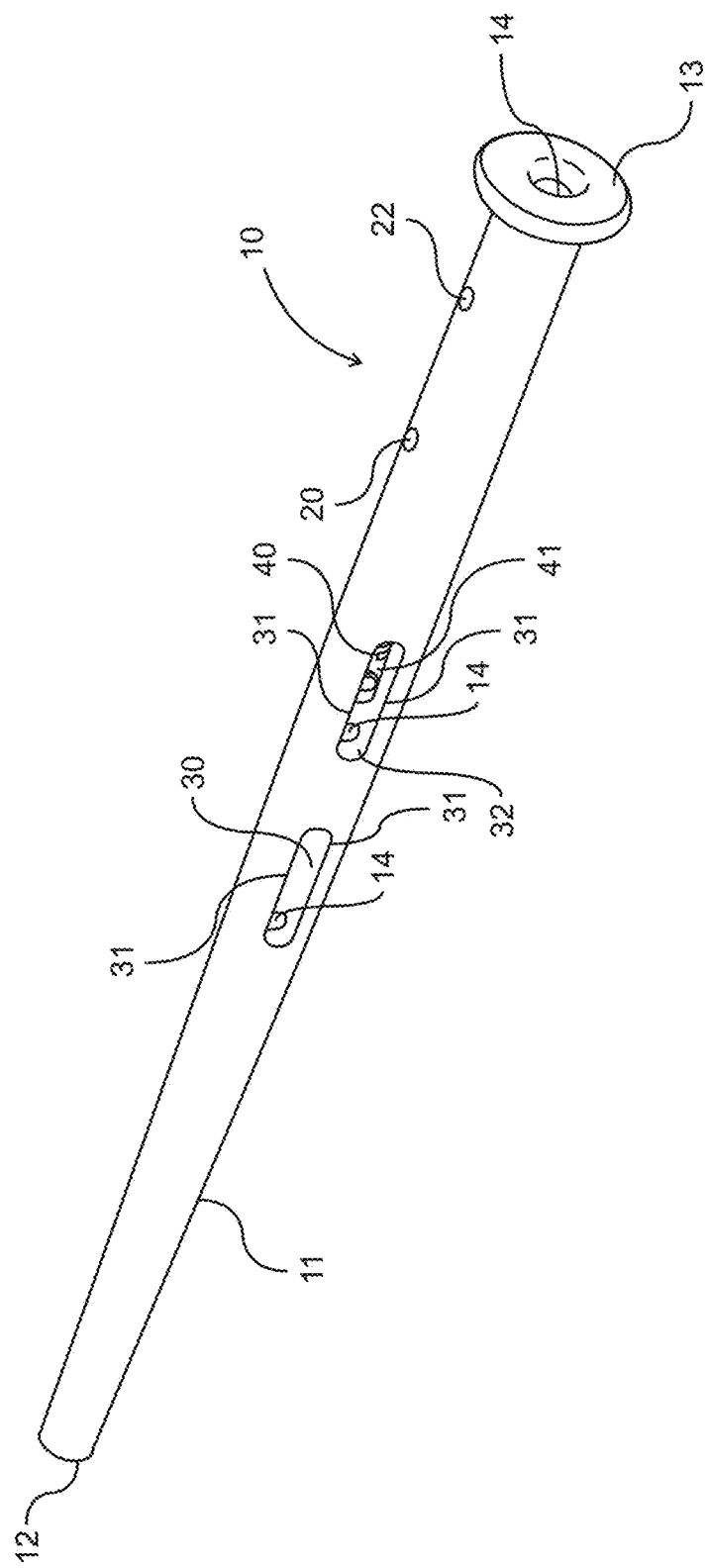
FIG. 5 is a perspective view of a nail and compression member according to the present invention.
Figure 6:
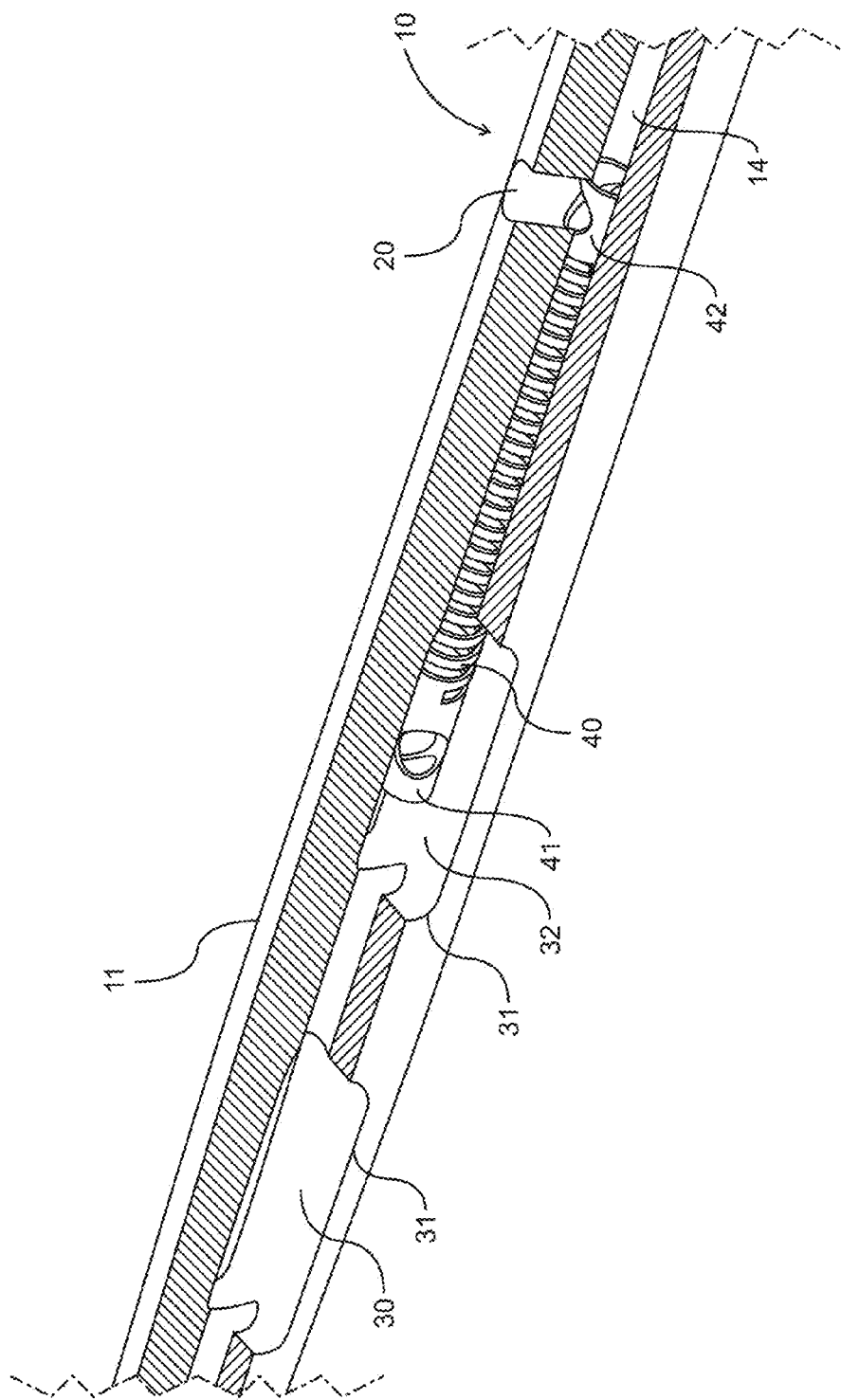
FIG. 6 is a partially cut-away view of a nail and compression member according to the present invention.

FIG. 4 shows a perspective view of the nail 10 shown in FIG. 2, showing an embodiment of the nail 10 in which the elongated apertures 30, 32 allowing dynamic movement of the nail 10 are at a ninety degree angle to the remaining distal apertures 20, 22 that lock the nail 10 to the bone when fasteners are inserted therethrough. In this embodiment, the axes 90 of the elongated apertures 30, 32 transversing the nail are substantially perpendicular to the axes 92 of the distal apertures 20, 22 transversing the nail. FIG. 5 shows another view of the embodiment of the nail 10 with a compression member 40, in this instance a spring, inserted within the nail 10. In this embodiment, both ends of the compression member 40 can engage a fastener that will transverse the nail 10 and pierce a portion of the bone. An end 41 of the compression member 40 is shown aligned with the second elongated aperture 32 of the nail 10. FIG. 6 is a cut-away image of the nail 10 showing an extension spring compression member 40 inside the nail 10, which can span the fusion site. This figure illustrates that the compression member 40 can have apertures 47, 48 through its first and second ends 41, 42, which can align with the substantially perpendicular axes 90, 92 of the second elongated aperture 32 and first distal aperture 20 in the nail 10.

Figure 7:
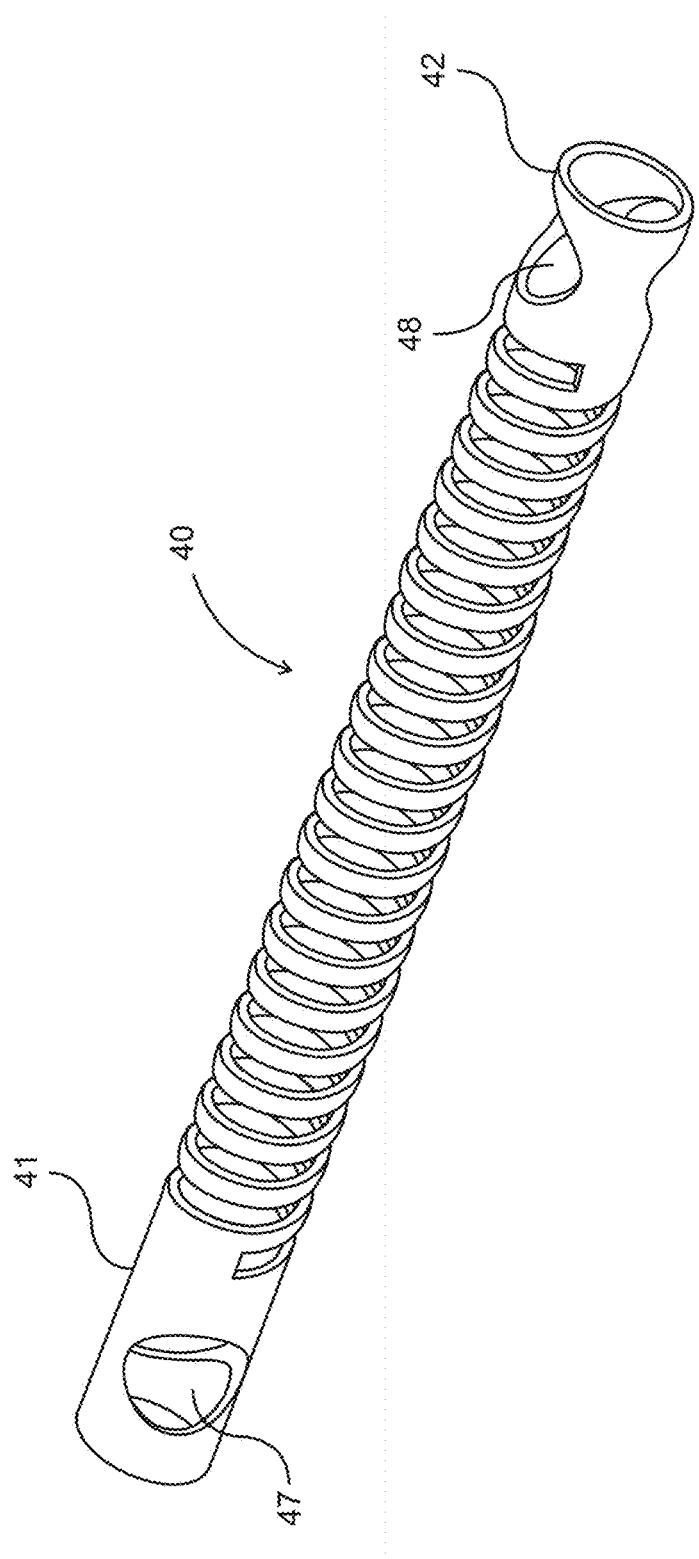
FIG. 7 is a perspective view of one embodiment of a compression member according to the present invention.

FIG. 7 illustrates one possible embodiment of a compression member 40, a spring that can be utilized to apply compressive force according to the invention. The spring can be an extension spring, compression spring, or torsional spring. An extension spring is compressed upon insertion into the nail 10 such that the spring will expand after insertion in the nail 10. A compression spring is expanded upon its insertion in the nail 10 such that it will compress after its insertion. Depending on the placement in the nail 10, a compression spring, expansion spring, or both types of springs can be utilized separately or together to apply create the compressive force for fusion.

At least one end 41, 42 of the compression member 40 can engage a fastener. For example, as shown in FIG. 7, the first and second ends 41, 42 of the compression member 42 include apertures 47, 48 therethrough. At least one of the ends 41, 42 of the compression member 40 align with at least one aperture 30, 32, 20 in the nail 10 so that the fastener can cross through one side of the nail 10, engage the compression member 40, and through the other side of the nail 10. The axes through the apertures 47, 48 at each end 41, 42 of the compression member 40 can be parallel or perpendicular to one another depending on the location of the apertures 30, 32, 20 in the nail 10 in which the compression member 40 will align. Various other mechanisms can be utilized to create the compressive force and the spring as shown is just one choice. In addition, the compression member 40 can engage the fastener in any manner known in the art and is not limited to the above-described engagement mechanism.

FIG. 8A illustrates a cross-sectional view of an alternate configuration of the nail 10. The compression member 40 can be inserted into the nail 10 with a first end 41 of the compression member 40 stopped at the proximal end 12 of the nail body 11 and the second end 42 of the compression member 40 engaged with a first locking fastener 50 which traverses the nail 10 at one of the elongated apertures 30, 32, e.g., the first elongated aperture 30 as shown in FIG. 8A. The nail 10 is surgically inserted such that the first fastener 50 is inserted into a bone on one side of a fusion site. A second fastener 51 can be inserted through a first 20 or second 22 distal aperture in the nail 10 that is located on the other side of the fusion site, such that the compression device creates a dynamic compressive force across the fusion site. A third and fourth fastener can be placed in the remaining elongated 32 and distal apertures 20, 22 to further anchor the nail 10 to the bone on each side of the fusion site or fracture.

FIG. 8B illustrates one embodiment of a compression spring 40 that can be utilized in the embodiment of the nail 10 shown in FIG. 8A. The compression spring 40 is shown (1) in an expanded state before insertion and (2) in a compressed state during insertion. The compression spring 40 would return to the expanded state during the healing process. An extension spring 40 has opposite effects, i.e., it would be compressed prior to insertion and expanded during insertion such that it would return to the compressed state during the healing process.

An embodiment of an insertion tool for placement of the compression member is shown in FIG. 8C. To insert a compression member into the nail 10, each compression member 40 may be pre-loaded or inserted on an insertion device 60 that includes a handle 62 and a rod 64 which can be inserted lengthwise into the nail 10. The rod 64 has a first end 65 projecting from the handle 62 and a second end 67 distal from the handle 62. The second end 67 of the rod 64 can engage the compression member 40. The second end can engage the first 41 and second 42 end of a compression member 40 as shown in FIG. 9C, or can engage one of the two ends 41, 42 as shown in FIG. 8C. A non-limiting example, shown in FIG. 8C, illustrates that at least one end 41, 42 of the compression member 40 can have a female threaded portion 43. The female threaded end 43 of the compression member 40 can be attached to a mail threaded portion 68 of an insertion device 60, or vice versa. In this embodiment, after the compression member 40 is inserted in the nail 10, the insertion device 60 can be simply unscrewed from the compression member 40.

A stop member 66 can project from the rod 64 of the insertion device 60 between the handle 62 and the attached compression member 40. When the compression member 40 is inserted into the nail 10, the stop member 66 can abut the distal end 13 of the nail 10, which marks the position in which at least one end 41, 42 of the compression member 40 is aligned with the desired corresponding one or more elongated and distal apertures in the nail body 11. The compression member 40 can be detached from the insertion device by either twisting the handle 62, pulling a trigger on the handle 62 which activates a cutting mechanism to cut the rod of the device, or by inserting a fastener through an end 41, 42 of a compression member 40, which breaks the attachment of the compression member to the rod 64 of the insertion device 60.

FIG. 9A shows another embodiment of the nail 10 illustrating a first fastener 50 in the proximal end 33 of a first elongated aperture 30 to anchor the nail 10 to a first side of a fusion site. A second fastener 51 can be inserted in a third distal aperture 24 to anchor the nail 10 to another side of the fusion site such that the desired site of compression is between the proximal 12 and distal 13 ends. The axis 92 of this third distal aperture 24 can parallel or perpendicular to the axes 90, 92 of the remaining apertures. For example, as shown in FIG. 9A, the axis 90 of the first oblong aperture 30 and the axis 92 of the third distal aperture 24 transversing the nail are parallel to each other and are perpendicular to the axis 90 of the second oblong aperture 32, the axis 92 of the first distal aperture 20, and the axis 92 of the second distal aperture 22 transversing the nail. A compression member 40 can be inserted such that its first end 41 can engage a third fastener at the proximal end 33 of the second elongated aperture 32 and the second end 42 of the compression member 40 can engage a third fastener transversing either the first 20 or second 22 distal aperture. As the healing process takes place, the fusion site will be under a dynamic compressive force between the second elongated aperture 32 and either the first 20 or second 22 distal aperture depending on which aperture is chosen. Upon compression, the nail will move such that the first fastener and third fastener will shift their positions from the proximal ends 33 to the distal ends 34 of the elongated apertures 30, 32.

FIG. 9B illustrates another embodiment of an insertion device for placement of a compression member 40 in the nail 10. In this embodiment, the rod 64 of the insertion device 60 is used to advance the compression member 40 into the nail 10. The compression member 40 and insertion device 60 can optionally be machined as one unit. When a first stop member 66 of the insertion device abuts the distal end 13 of the nail 10, the one or more ends 41, 42 of the compression member 40 are aligned with the corresponding one or more elongated 30, 32 or distal 20, 22 apertures in the nail body 11. After engaging a first end 41 of the compression member 40 with a first fastener within the nail 10, the compression member is loaded by manual distraction. A second stop member 68 of the insertion device 60 engages either the end 13 of the nail 10 or a corresponding structure in the nail 10 such as a hole or groove, marking the position in which the second end of the compression member is aligned with a corresponding aperture or groove formed in the inner channel 14 of the nail 10. After inserting a second fastener into the second end 42 of the compression member 40 and through the nail 10, thereby locking the compression member 40 in a loaded position, the handle 62 can be rotated in a clockwise or counter-clockwise motion. The rotation detaches the handle 62 of the insertion device 60 from the compression member 40 at a position on the insertion device 60 between the handle 62 and second end 42 of the compression member. The precise position in which the insertion device 60 is broken to remove it from the nail 10 can be a previously stressed or scored position to allow easy breakage. The insertion device 60 can also use a releasable connecting member 70 to attach and detach from the compression member 40.

Figure 10:
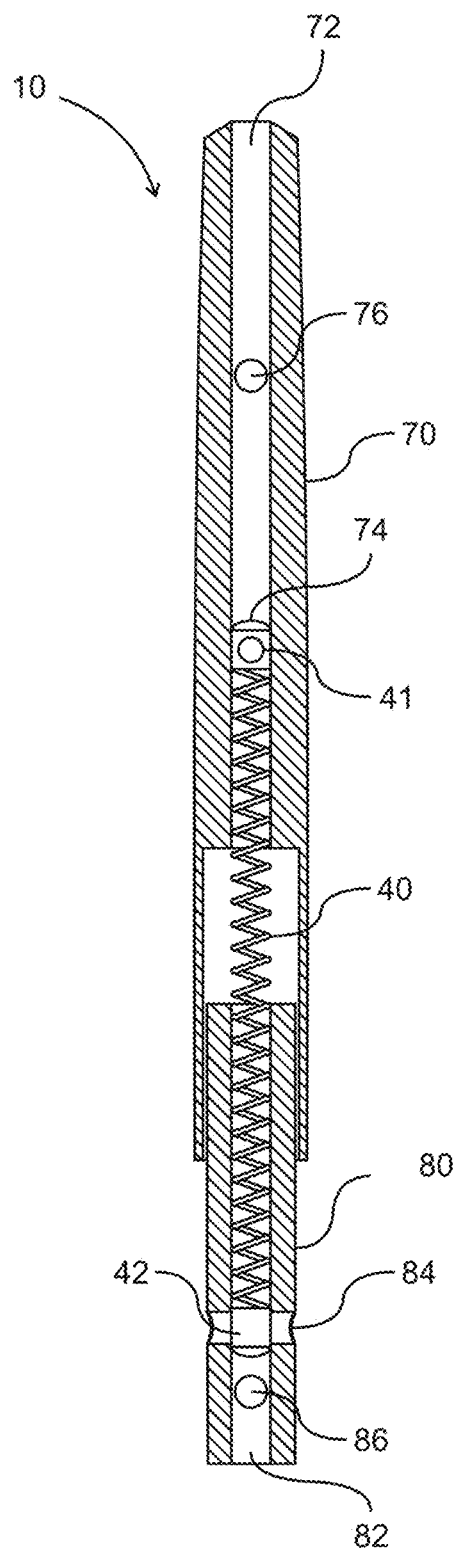
FIG. 10 is a perspective view of an embodiment of a telescopic nail according to the present invention.

As shown in FIG. 10, the nail 10 may be telescopic. In this embodiment, the nail 10 can be inserted in an extended position and the nail 10 would effectively shorten as the fusion site reabsorbs and compression takes place. The nail 10 can be used with a jig device to keep one or more of the bone sections secured and provides alignment for insertion of the nail 10 and the transverse insertion and placement of the required fasteners.

In this telescopic embodiment, the nail 10 has an elongated body 11 having two independent body sections. The body sections comprise a proximal section 70 and a distal section 72, wherein the distal section 72 is at least partially contained within the proximal section 70. The proximal section 70 has an inner channel 72 and at least one aperture 74 capable of permitting a fastener to pass through the proximal section 70 and be secured in a position transversing the nail 10. The distal section 80 also has an inner channel 82 and at least one aperture 84 capable of permitting a fastener to pass through the distal section 80 and be secured in a position transversing the nail 10.

A compression member 40 can be inserted inside the channels 72, 82 such that the compression member 40 is contained within both the inner channel 72 of the proximal section 70 and the inner channel 82 of the distal section 80. The first end 41 of the compression member 40 is capable of engaging a fastener received in the aperture 74 formed through the proximal section 70 and the second end 42 of the compression member 40 is capable of engaging a fastener received in the aperture 84 of the distal section 80. The compression member 40 can exert a force to move the proximal section 70 and distal section 80 toward one another. Thus, the nail 10 can thereby provide compression to a fusion or fracture site when at least one fastener is received in the aperture 74 of the proximal section 70 on one side of the fusion or fracture site and at least one fastener is received in the aperture 84 of the distal section 80 on an opposing side of the fusion or fracture site.

As shown in FIG. 10, the nail can have more than one aperture in each of the proximal and distal sections 70, 80. The axes of the apertures transversing the nail body sections can be parallel to one another, perpendicular to one another, or a combination of both parallel and perpendicular depending on the amount of stabilization desired. In alternative embodiments, the compression member 40 and proximal section 70 can be formed as one unit or the compression member 40 and distal section 80 can be formed as one unit.

Figure 11:
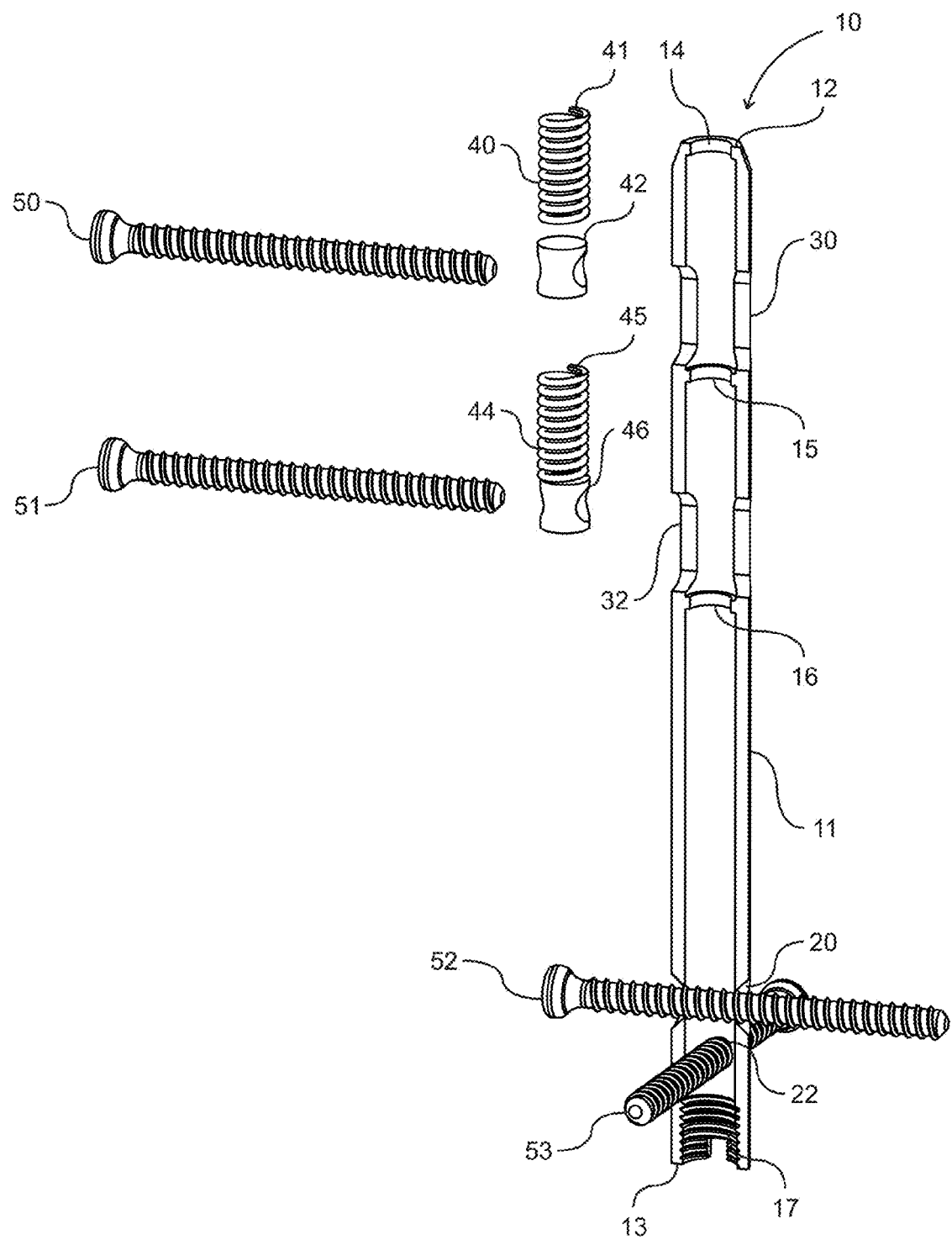
FIG. 11 is a partially cut-away view of the nail according to the present invention.
Figure 12:
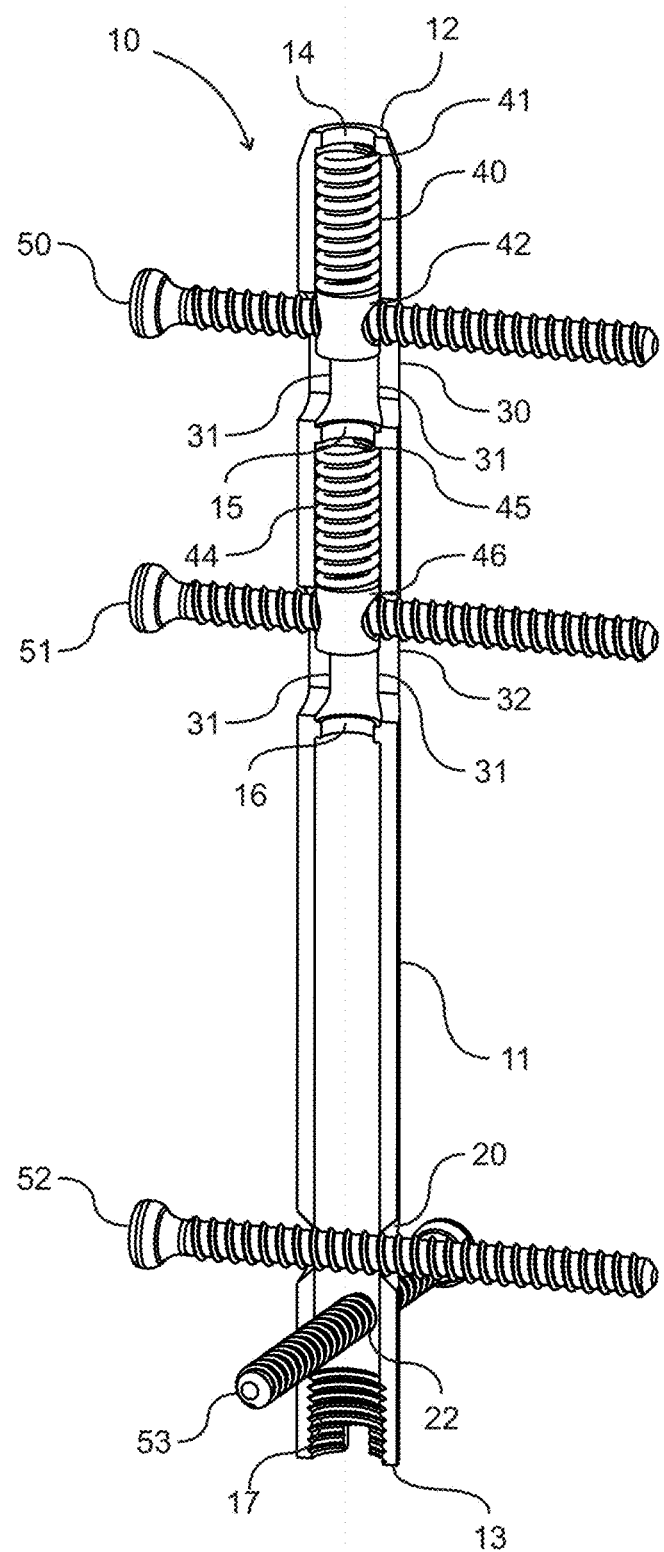
FIG. 12 is a partially cut-away view of the nail shown in FIG. 11 in which the compression member is compressed according to the present invention.
Figure 13:
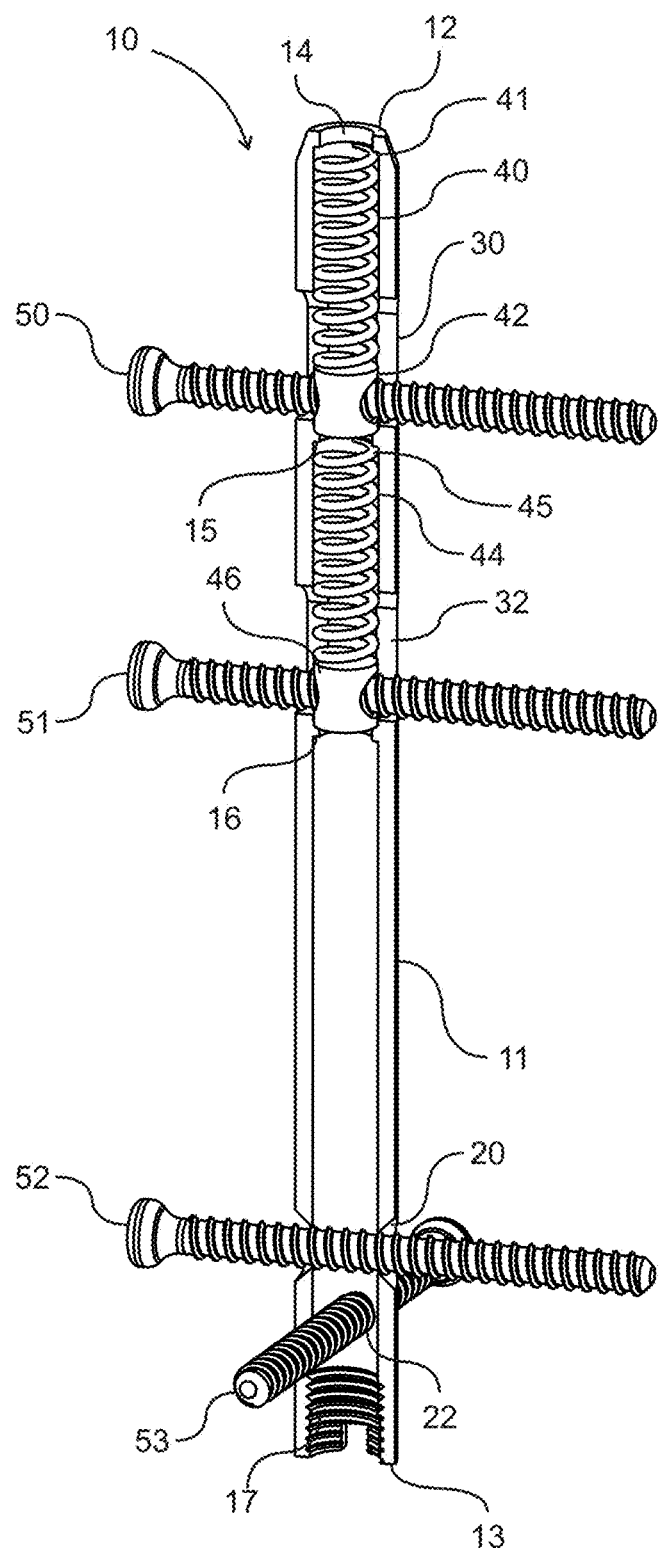
FIG. 13 is a partially cut-away view of the nail shown in FIG. 11 in which the compression member is expanded according to the present invention.
Figure 14:
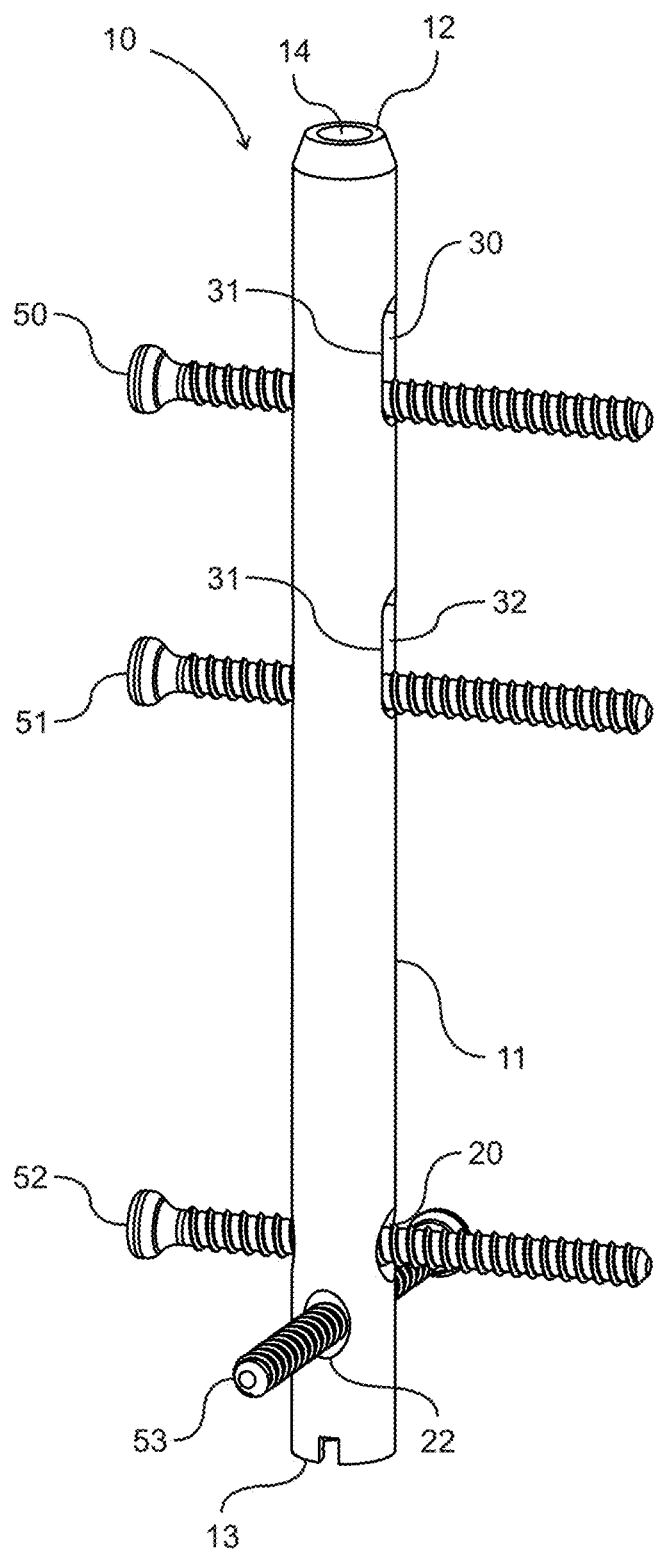
FIG. 14 is a perspective view of a nail shown in FIG. 11 according to the present invention.

FIGS. 11-14 show an embodiment of the nail 10 utilizing two compression members 40, 44 in sequence. Both the first 40 and second 44 compression member push the nail 10 such that the nail 10 slides over the first 30 and second 32 elongated apertures to effectively apply compression on a fusion site between the second elongated aperture 32 and the first distal aperture 20 of the nail 10. This embodiment includes a projection 15, for example a ridge or inner ring, that is within the inner channel 14 of the nail 10 and between the first 30 and second 32 elongated apertures. The projection 15 can be independent of the nail and inserted within the nail 10 or can be manufactured as part of the nail 10. Thus, a compression member 40 aligned with the first elongated aperture 30 and a second compression member 44 aligned with the second elongated aperture 32 can provide additional compression. A first fastener 50 and a second fastener 51 are aligned and engaged with the second end 42, 46 of each compression member 40, 44 and transverse the nail 10. FIG. 11 illustrates an embodiment in which an end 42, 46 of the compression member 40, 44 engaging the fastener 50, 51 can either be attached to the compression member 40, 44, or independent of the compression member 40, 44. The first compression member 40 will exert a compressive force on the proximal end 12 of the nail 10, while the second compression member 44 will exert a compressive force on the projection 15 between the first and second elongated apertures 30, 32. Both compression members will move the nail 10 along the first and second fasteners 50, 51 to provide compression to the fusion site that is between the proximal, dynamic portion of the nail 10 and the distal, static portion of the nail 10 held by one or more fasteners.

Though a second projection 16 is shown between the second elongated aperture 32 and the distal end 13 of the nail 10, the additional projection 16 is not required to accomplish the above-described compression mechanism. However, in this embodiment the compression members can be pre-loaded in the nail 10 and in such an embodiment the projections 15, 16 can keep the pre-loaded compression members in place. In alternative embodiments, the first compression member 40 can have a slightly smaller diameter than the projection 15 in the inner channel 14 of the nail 10 so that the compression member 40 can be inserted during the surgical procedure. In another embodiment, the projection 15 can be inserted after the placement of the first compression member 40.

The embodiments shown in FIG. 11-14 also show a distal end 13 of the nail 10 having a threaded portion 17, in which a corresponding threaded end cap may be attached. When utilizing an end cap with the distal end 13 of the nail 10, the end cap need not utilize a threaded attachment means, but can be designed to fit the end of the nail 10 by a snap fit, screw fit, or in any other manner known in the art.

Figure 15:
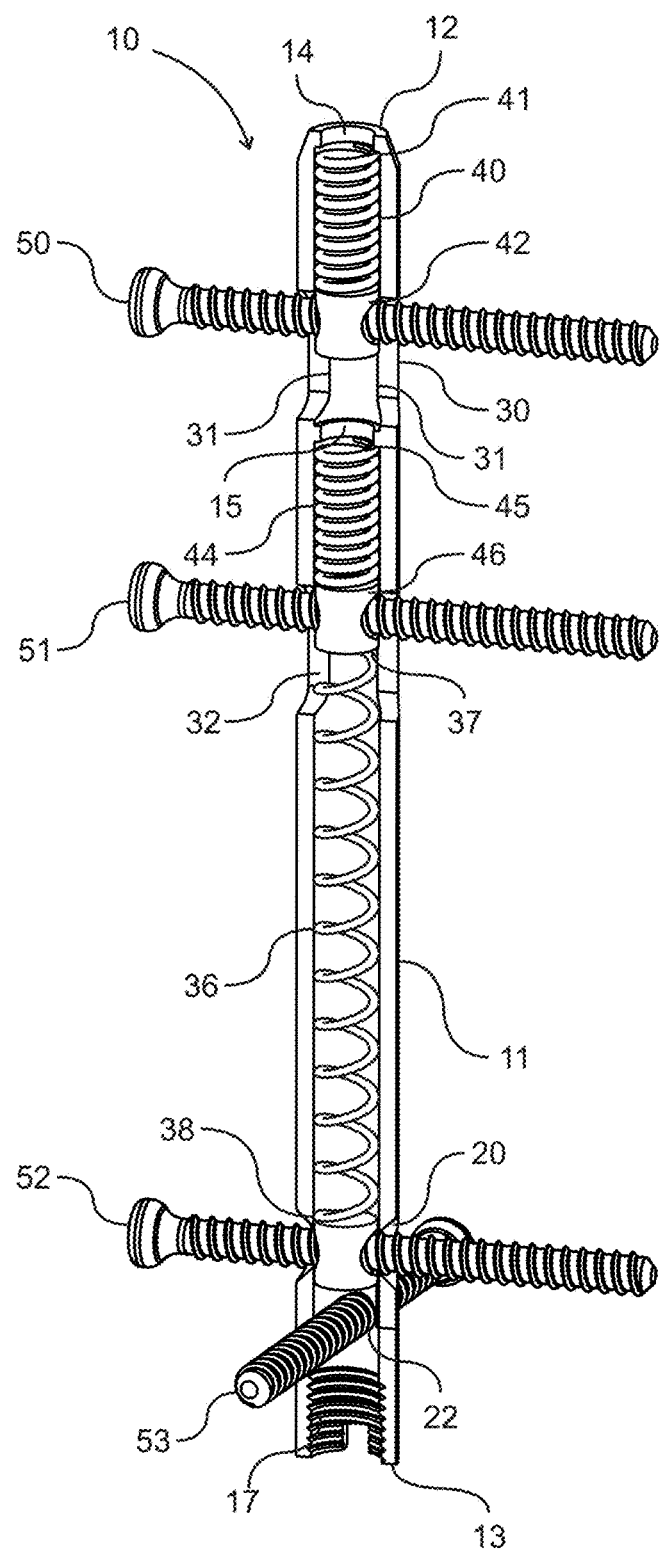
FIG. 15 is a partially cut-away view of a nail according to the present invention.

In another embodiment shown in FIG. 15, the nail 10 can employ three compression members 40, 44, 36. In this embodiment, the nail 10 has a first 20 and a second 22 distal aperture and a first 30 and a second elongated aperture 32. A first projection 15 is located within the inner channel 14 between the first elongated aperture 30 and the second elongated aperture 32. The first end 41 of the first compression member 40 abuts the proximal end 12 of the nail 10 and the second end 42 of the first compression member 40 is capable of engaging a fastener 50 received in the first elongated aperture 30. The first end 45 of the second compression member 44 abuts the first projection 15 and the second end 46 of the second compression member 44 is capable of engaging a fastener 51 received in the second elongated aperture 32. The first end 37 of the third compression member 36 is capable of engaging the fastener 51 received in the second elongated aperture 32, i.e., the same fastener 51 that is engaged with the second end 46 of the second compression member 44. For example, the second compression mechanism 44 can push on the fastener 51 in one direction while the third compression member 36 can pull on the fastener 51 in the same direction when the second compression member 44 is a compression spring and the third compression mechanism 36 is an extension spring. The second end 38 of the third compression member 36 is capable of engaging a fastener 52 received in the first distal aperture 20. All three compression members 40, 44, 36 exert a force to move the nail 10 and thereby provide compression to a fusion or fracture site.

When employed as a total system, the invention can include guide wires for insertion and initial placement of nail 10 (ball tipped and smooth), flexible reamers, a measuring device, an alignment and insertion jig, intramedullary nails 10 of various sizes, implantable mechanical compression devices (for example compression, extension or torsion springs, biocompatible elastic bands, Belleville washers, etc), a compression device insertion tool, a transfixion compression pin, transfixion interlocking fasteners with relative drills, drill guides and depth gauges, an end cap and a retrieval device with a slap hammer.

The procedural steps for, but not limited to, a tibial talo calcaneal fusion may be as follows. The tibial, talar, and calcaneal joint surfaces, fusion or fracture sites are prepared and reduced in a manner known in the art. A guide wire for nail 10 insertion is inserted across the site of repair, from the intended insertion site of the nail 10. Placement of the guide wire is confirmed with fluoroscopy. The bone/medullary canal is sequentially reamed using flexible cannulated reamers to the appropriate size, approximately 0.5-1.0 millimeter greater than the diameter of the widest, generally the trailing, portion of the nail 10. For embodiments in which the nail 10 has an irregular cross-sectional shape, the insertion procedure will include steps which will follow the initial drilling and reaming that is described above, in which a final shape for the nail 10 is created using a shaped broach, oval drill or small round drill off-centered with a specialized drill guide.

The nail 10 is attached to a jig and inserted into the bone, across the fusion site using a mallet if necessary. The guide wire is removed. A mallet can be used to tap the trailing end of the jig to gain initial compression. A transfixion compression pin is inserted across the tibia, proximal to the leading edge 12 of the nail 10. External fine compression is adjusted by turning the knobs on both sides of the jig.

For insertion and use of one compression member 40, such as an extension spring, the following procedural steps are provided. The appropriate strength compression member 40, e.g., a spring, elastic band, etc., is inserted using an insertion device 60 through the inner channel 14 in the nail 10. The insertion tool 60 is designed to stop at a position in which the leading end 41 of the compression member 40 is in the appropriate position corresponding with the central most elongated hole 32 of the nail 10.

A fastener is inserted into and across the bone such as the tibia, from medial to lateral, and through the nail 10 in the second, central most elongated hole 32 using the jig, thereby engaged with the first end 41 in the leading edge of the compression member 40 and securing the end 41 of the compression member 40 at that position. The second, locking fastener has a dynamic effect in that it can change position in the second elongated aperture 32 upon compression.

A fastener can be inserted into and across the bone such as the tibia, from medial to lateral, and through the nail 10 in the proximal end 33 of the first, outer most elongated hole 30 using the jig. This fastener has a dynamic effect in that it can change position in the first elongated aperture 30 upon compression. The jig precisely places the fastener in the most proximal end 33 of the elongated aperture 30 to allow travel for later compression.

The jig is rotated 90 degrees medially to posterior, and snaps into position. The compression member 40 is loaded by distracting with the insertion tool 60. The insertion tool is designed to stop at the appropriate position, thereby aligning the distal end 42 of the compression member 40 with the central most round distal hole 20 in the nail 10. A fastener is inserted from posterior to anterior into the calcaneus, through the first, central-most distal aperture 20 of the nail 10, thereby capturing and securing the compression member 40 in the locked position. This locking fastener is static in that it does not change its position in the nail 10. In alternative embodiments, the fastener is inserted from medial to lateral or at an oblique angle.

A fastener can be inserted posterior to anterior, into and across the calcaneus, through the second, outer most distal aperture 22, using the jig. This locking fastener is static in that it does not change its position in the nail 10. In alternative embodiments, the fastener is inserted from medial to lateral or at an oblique angle. The jig is detached and removed from the operative field. In certain embodiments, an end cap is inserted into the distal end 13 of the nail 10. The wounds are closed and the extremity dressed and splinted in the usual fashion.

For the insertion and use of two compression members, such as one compression spring type compression member 40 and one extension spring type compression member 40, the following steps are provided. The same steps as those described above for insertion of one compression member are followed, up to the step of adjusting the external fine compression and prior to inserting the appropriate compression member.

Next, a first compression member 40, such as a compression spring, is selected and inserted through the inner channel 14 in the nail 10. The first compression member 40 is loaded against the proximal end 12 of the nail 10. A first locking fastener 50 is inserted into and across the bone, from medial to lateral, and through the nail 10 in the proximal end of the first, proximal most elongated hole 30, engaging with the second, trailing end 42 of the first compression member 40 and thereby securing the second end 42 of the compression member 40. A second compression member 44, such as an extension spring, is selected and inserted through the inner channel 14 in the nail 10 using an insertion device 60 as described in the above procedure. A second locking fastener is inserted into and across the bone, from medial to lateral, and through the nail 10 in the second, inner most elongated aperture 32, engaging with the first, leading end 45 of the second compression member 44. The second compression member 44 is loaded by extending or stretching the second compression member 44. The distal, second end 46 of the second compression member 44 is aligned with the first, central most, distal aperture 20 of the nail 10. A third locking fastener 52 is inserted from posterior to anterior into the bone, through the first distal aperture 20 of the nail 10 and engaging with the second end 46 of the second compression member 44, thereby securing the second compression member 44 in an extended, loaded and locked position. In alternative embodiments, the third fastener can be inserted from medial to lateral or at an oblique angle. A fourth locking fastener 53 can be inserted lateral to medial, into and across the bone and through the second, outer most, distal aperture 22 of the nail 10. In alternative embodiments, the fourth fastener 53 can be inserted from posterior to anterior or at an oblique angle.

In an embodiment using two compression spring type compression members 40, 44, a first compression member 40, such as a compression spring, is selected and inserted through the inner channel 14 in the nail 10. The first compression member 40 is loaded against the proximal end 12 of the nail 10. A first locking fastener 50 is inserted into and across the bone, from medial to lateral, and through the nail 10 in the proximal end of the first, proximal most elongated hole 30, engaging with the second, trailing end 42 of the first compression member 40 and thereby securing the second end 42 of the compression member 40. A second compression member 44, such as a compression spring, is selected and inserted through the inner channel 14 in the nail 10. The second compression member 44 is loaded against a projection 15 between the first elongated aperture 30 and second elongated aperture 32 in the nail 10. A second locking fastener 51 is inserted into and across the bone, from medial to lateral, and through the nail 10 in the proximal end 33 of the second elongated hole 32, engaging with the second, trailing end 46 of the second compression member 44 and thereby securing the second end 46 of the compression member 44. A third fastener 52 and a fourth fastener 53 can be inserted in the first and second distal apertures 20, 22.

Because this embodiment utilizes a projection 15 within the inner channel 14 of the nail 10, in this embodiment the first compression member can be pre-loaded in the nail 10. In alternative embodiments, the first compression member 40 can have a slightly smaller diameter than the projection 15 in the inner channel 14 of the nail 10 so that the compression member 40 can be inserted during the surgical procedure. In another embodiment, the projection 15 can be inserted after the placement of the first compression member 40. The nail 10 can include a groove or a similar structure in the inner channel 14 to guide insertion of the projection 15.

Optionally a method including steps for inserting a third compression member 36 such as an extension spring in addition to the method for using a first compression spring 40 and a second compression spring 44 is described as follows. After the second compression member 44 is loaded against a projection 15 between the first elongated aperture 30 and second elongated aperture 32 in the nail 10 and before the second fastener 51 is inserted, a third compression member 36 can be loaded distal to the second compression member 44. Both the second end 46 of the second compression member 44 and the first end 37 of the third compression member 36 can align with the proximal end 33 of the second elongated aperture 32. A second fastener 51 is inserted through the proximal end 33 of the second elongated aperture 32 and is engaged with both the second compression member 44 and the third compression member 36. In one embodiment, the second fastener 51 can engage the third compression member 36 via an aperture 47 in a first end 37 of the third compression member 36 such that the second fastener 51 is received through the aperture 47. The second compression member 44 can engage the second fastener 51 by its mere abutment with the second fastener 51 at its second end 46, i.e., if the second compression member 44 includes an aperture 48 through its second end 46, the second compression member 44 need not engage the fastener 51 by receiving the fastener through its aperture 48. Once the second compression member 44 is inserted in the nail, the third compression member 36 can be inserted and push the second compression member 44 toward the proximal end 12 of the nail 10. The second fastener 51 can engage an aperture 47 in the first end 37 of the third compression member and thereby "sandwich" the second compression member 44 between the projection 15 within the nail 10 and the second fastener 51 or first end 37 of the third compression member 36 in the second elongated aperture 32.

The third compression member 36 is loaded by extending or stretching the third compression member 36. The distal, second end 38 of the third compression member 36 is aligned with the first, central-most, distal aperture 20 of the nail 10. A third locking fastener 52 is inserted through the first distal aperture 20 of the nail 10 and engaging with the second end 48 of the third compression member 36, thereby securing the third compression member 36 in an extended, loaded and locked position. A fourth locking fastener 53 can be inserted into and across the bone and through the second, outer most, distal aperture 22 of the nail 10.

This invention may be industrially applied to orthopedic surgeries to provide continuous dynamic compression for the fixation of bone fractures and fusion sites across the healing site throughout all stages of the healing process. While the present invention has been described regarding particular embodiments, it is recognized that additional variations of the present invention may be devised without departing from the inventive concept. A person skilled in the art would appreciate that exemplary embodiments described hereinabove are merely illustrative of the general principles of the present invention and not meant to be a limitation thereof. Other components, configurations, modifications or variations may be employed that are within the scope of the invention.

All terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. The term "adapted to" is drawn to a capability. Thus, it is intended that the invention cover all embodiments and variations thereof as long as such embodiments and variations come within the scope of the appended claims and their equivalents.

What is claimed is:

1. An intramedullary nail for providing dynamic compression across a fusion or fracture site, comprising:
   an elongated body having a proximal end, a distal end, and an inner channel;
   at least one distal aperture located proximate to said distal end of said body and which is capable of permitting a fastener to pass therethrough and be secured in a position transversing said nail,
   at least one elongated aperture having interior sides located closer to said proximal end of said body than said distal aperture and which is capable of receiving a fastener that transverses said nail such that said nail may have a movement relative to said fastener, said movement restricted by said interior sides of said at least one elongated aperture,
   at least one compression member contained within said inner channel, said at least one compression member having a first end and a second end, and at least one of said ends of said at least one compression member having a compression member aperture therethrough, said compression member aperture substantially aligned with said at least one elongated aperture, said compression member aperture capable of engaging said fastener received in said elongated aperture, wherein said at least one compression member is capable of exerting a force against at least one of said fastener and said interior side of said at least one elongated aperture thereby causing said nail to move relative to said fastener, said at least one compression member fully enclosed within said inner channel;
   wherein said at least one compression member comprises a first and a second compression member;
   wherein said first compression member is selected from the group consisting of a compression spring, a torsional spring, a Belleville washer, and a plurality of Belleville washers; and
   wherein said second compression member is selected from the group consisting of a compression spring, a torsional spring, a Belleville washer, and a plurality of Belleville washers;
   thereby increasing compression to said fusion or facture site when at least one fastener is received in said elongated aperture on one side of said fusion or fracture site, and at least one fastener is received in said distal aperture on an opposing side of said fusion or fracture site.

2. The intramedullary nail of claim 1, wherein:
   said at least one distal aperture comprises a first and a second distal aperture;
   said at least one elongated aperture comprises a first and a second elongated aperture;
   a projection, wherein said projection is located within said inner channel between said first elongated aperture and said second elongated aperture;
   said first end of said first compression member abuts said proximal end of said nail and said second end of said first compression member is capable of engaging a fastener received in said first elongated aperture;
   said first end of said second compression member abuts said projection and said second end of said second compression member is capable of engaging a fastener received in said second elongated aperture;

whereby both said first and second compression member exert a force to move said nail and thereby provide compression to a fusion or fracture site located between said first distal aperture and said second elongated aperture when said fasteners are received in said nail.

3. The intramedullary nail of claim 2, wherein:
said at least one compression member further comprises a third compression member having a first end and a second end;
said first end of said third compression member is capable of engaging said fastener received in said second elongated aperture and said second end of said third compression member is capable of engaging a fastener received in said first distal aperture;
whereby said first, second, and third compression member exert a force to move said nail and thereby provide compression to a fusion or fracture site located between said first distal aperture and said second elongated aperture when said fasteners are received in said nail.

4. The intramedullary nail of claim 3, further comprising at least three fasteners, wherein a first fastener is both engaged with said second end of first compression member and is received in said first elongated aperture, a second fastener is both engaged with said second end of said second compression member and said first end of said third compression member and is received in said second elongated aperture, and a third fastener is both engaged with said second end of said third compression member and is received in said first distal aperture.

5. The intramedullary nail of claim 2, further comprising at least three fasteners, wherein a first fastener is both engaged with said second end of said first compression member and is received in said first elongated aperture, a second fastener is both engaged with said second end of said second compression member and is received in said second elongated aperture and a third fastener is received in said first distal aperture.

6. The intramedullary nail of claim 1, wherein said first end of said at least one compression member abuts said proximal end of said nail and said second end of said compression member is capable engaging a fastener received in one of said at least one elongated aperture,
whereby said compression member exerts a force to move said nail and thereby provide compression to a fusion or fracture site located between said at least one distal aperture and said elongated aperture when said fasteners are received in said nail.

7. The intramedullary nail of claim 1, wherein said first end of said at least one compression member is capable of engaging a fastener received in one of said at least one elongated aperture and said second end of said at least one compression member is capable of engaging a fastener received in one of said at least one distal aperture;
whereby said at least one compression member exerts a force to move said nail and thereby provide compression to a fusion or fracture site located between said distal aperture and said at least one elongated aperture when said fasteners are received in said nail.

8. The intramedullary nail of claim 7, wherein said at least one compression member is selected from the group consisting of an extension spring, biocompatible rubber, compressed gas compartment, elastic band, and stretch-activated compression member.

9. The intramedullary nail of claim 1, further comprising at least two fasteners, wherein at least one fastener is received in said at least one distal aperture and at least one fastener is both engaged with said at least one compression member and is received in said at least one elongated aperture.

10. The intramedullary nail of claim 1, wherein at least one of said ends of said compression member is capable of engaging said fastener received at an oblique angle in said distal aperture.

11. The intramedullary nail of claim 1, wherein said elongated body has a cross-sectional shape to prevent rotation of said nail, said cross-sectional shape is selected from the group consisting of an oval, triangle, cruciate shape, partially oval, clover shape, star shape, trapezoidal, rhomboid, and irregular geometric shape.

12. An intramedullary nail for providing dynamic compression across a fusion or fracture site, comprising:
an elongated body having a proximal end, a distal end, and an inner channel;
at least one distal aperture located proximate to said distal end of said body and which is capable of permitting a fastener to pass therethrough and be secured in a position transversing said nail, wherein said at least one distal aperture comprises a first and a second distal aperture;
at least one elongated aperture having interior sides located closer to said proximal end of said body than said distal aperture and which is capable of receiving a fastener that transverses said nail such that said nail may have a movement relative to said fastener, said movement restricted by said interior sides of said elongated aperture, wherein said at least one elongated aperture comprises a first and a second elongated aperture;
a projection, wherein said projection is located within said inner channel between said first elongated aperture and said second elongated aperture;
at least one compression member contained within said inner channel, said compression member having a first end and a second end, and at least one of said ends of said compression member is capable of engaging said fastener received in said elongated aperture, wherein said compression member is capable of exerting a force against at least one of said fastener and said interior side of said elongated aperture thereby causing said nail to move relative to said fastener, wherein said at least one compression member comprises a first and a second compression member;
said first end of said first compression member abuts said proximal end of said nail and said second end of said first compression member is capable of engaging a fastener received in said first elongated aperture;
said first end of said second compression member abuts said projection and said second end of said second compression member is capable of engaging a fastener received in said second elongated aperture;
whereby both said first and second compression member exert a force to move said nail and thereby provide compression to a fusion or fracture site located between said first distal aperture and said second elongated aperture when said fasteners are received in said nail;
wherein said first compression member is selected from the group consisting of a compression spring, a torsional spring, a Belleville washer, and a plurality of Belleville washers; and said second compression member is selected from the group consisting of a compression spring, a torsional spring, a Belleville washer, and a plurality of Belleville washers;

thereby increasing compression to said fusion or facture site when at least one fastener is received in said elongated aperture on one side of said fusion or fracture site, and at least one fastener is received in said distal aperture on an opposing side of said fusion or fracture site.

* * * * *